United States Patent
Burdorff et al.

(10) Patent No.: US 8,821,410 B2
(45) Date of Patent: Sep. 2, 2014

(54) BIOPSY DEVICE

(75) Inventors: Mark A. Burdorff, Loveland, OH (US); John A. Hibner, Mason, OH (US); Daniel F. Dlugos, West Chester, OH (US); Scott A. Gleason, Oshkosh, WI (US); Brian W. Schmidt, Neenah, WI (US)

(73) Assignee: Devicor Medical Products, Inc., Cincinnati, OH (US)

(*) Notice: Subject to any disclaimer, the term of this patent is extended or adjusted under 35 U.S.C. 154(b) by 105 days.

(21) Appl. No.: 13/429,489

(22) Filed: Mar. 26, 2012

(65) Prior Publication Data
US 2012/0209142 A1 Aug. 16, 2012

Related U.S. Application Data

(62) Division of application No. 12/412,435, filed on Mar. 27, 2009, now Pat. No. 8,167,816, which is a division of application No. 10/428,561, filed on May 2, 2003, now Pat. No. 7,510,534, which is a division of application No. 09/910,581, filed on Jul. 20, 2001, now Pat. No. 6,585,664.

(51) Int. Cl.
*A61B 10/00* (2006.01)
*A61B 17/32* (2006.01)

(52) U.S. Cl.
USPC .................. 600/564; 600/566; 606/167

(58) Field of Classification Search
USPC ............... 600/562–568; 604/164.01, 164.11; 607/167, 170, 171, 180
See application file for complete search history.

(56) References Cited

U.S. PATENT DOCUMENTS

| | | | |
|---|---|---|---|
| 4,567,896 A * | 2/1986 | Barnea et al. ............. | 600/443 |
| 5,526,822 A | 6/1996 | Burbank et al. | |
| 5,649,547 A | 7/1997 | Ritchart et al. | |
| 5,685,840 A | 11/1997 | Schechter et al. | |
| 5,690,660 A | 11/1997 | Kauker et al. | |
| 5,769,086 A | 6/1998 | Ritchart et al. | |
| 5,775,333 A | 7/1998 | Burbank et al. | |
| 6,007,497 A | 12/1999 | Huitema | |
| 6,017,316 A | 1/2000 | Ritchart et al. | |
| 6,086,544 A | 7/2000 | Hibner et al. | |
| 6,102,926 A | 8/2000 | Tartaglia et al. | |

(Continued)

OTHER PUBLICATIONS

U.S. Appl. No. 08/825,899, filed Apr. 2, 1997.

(Continued)

*Primary Examiner* — Max Hindenburg
*Assistant Examiner* — Jonathan M Foreman
(74) *Attorney, Agent, or Firm* — Frost Brown Todd LLC

(57) ABSTRACT

A method is provided for calibrating a surgical biopsy system. The biopsy system includes a biopsy instrument and control unit. The biopsy instrument includes a piercer, rotatable cutter, and a port for receiving tissue samples. The method comprises the steps of translating the cutter distally until the translation of the cutter is stopped at an extended position and recording the extended position. The cutter is then translated from the extended position proximally until the translation of the cutter is stopped at a retracted position proximal to the extended position. The retracted position is recorded. The method further comprises the step of rotating the cutter to a rotation speed while the cutter is located at the retracted position and, if determined that the rotation speed is within a predetermined rotation speed range, a feedback signal is provided on the display allowing the operator to progress to the next procedural step.

9 Claims, 20 Drawing Sheets

(56) References Cited

U.S. PATENT DOCUMENTS

| | | |
|---|---|---|
| 6,120,462 A | 9/2000 | Hibner et al. |
| 6,228,039 B1 | 5/2001 | Binmoeller |
| 6,273,862 B1 | 8/2001 | Privitera et al. |
| 6,428,487 B1 | 8/2002 | Burdorff et al. |
| 6,432,065 B1 | 8/2002 | Burdorff et al. |
| 6,585,664 B2 | 7/2003 | Burdorff et al. |
| 6,770,070 B1 * | 8/2004 | Balbierz .................. 606/41 |
| 7,510,534 B2 | 3/2009 | Burdorff et al. |
| 8,167,816 B2 | 5/2012 | Burdorff et al. |
| 2001/0011156 A1 * | 8/2001 | Viola et al. .................. 600/568 |

OTHER PUBLICATIONS

U.S. Appl. No. US 60/222,416, filed Aug. 2, 2000.
U.S. Appl. No. 08/825,899, filed Apr. 1997, Ritchart et al.

* cited by examiner

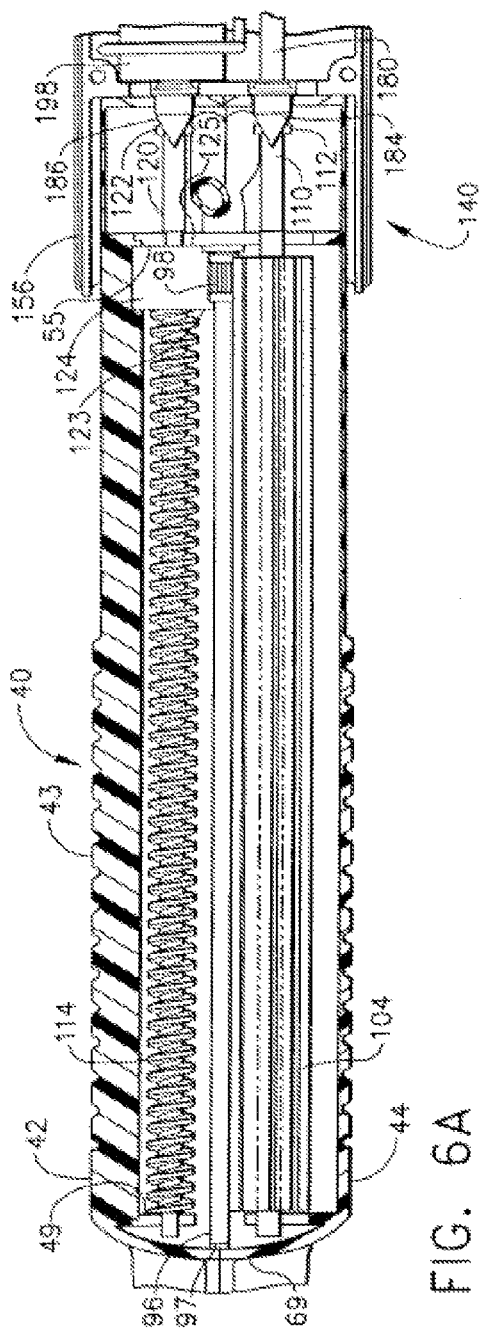
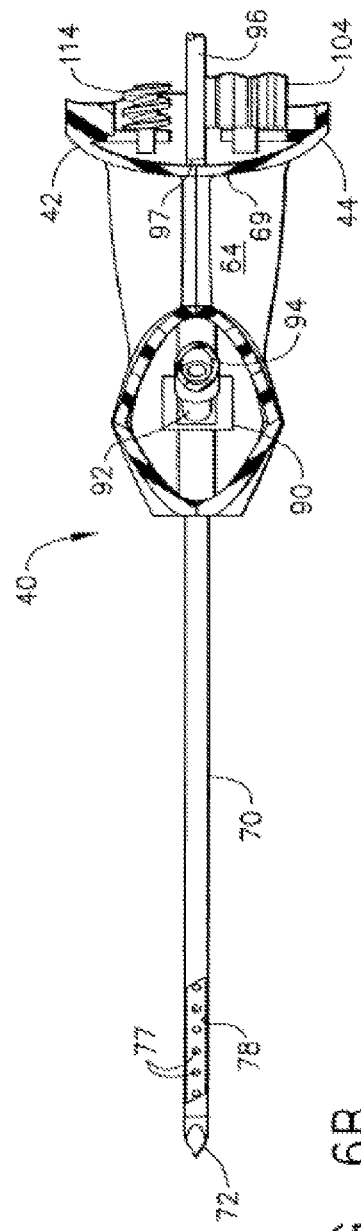
FIG. 6A
FIG. 6B

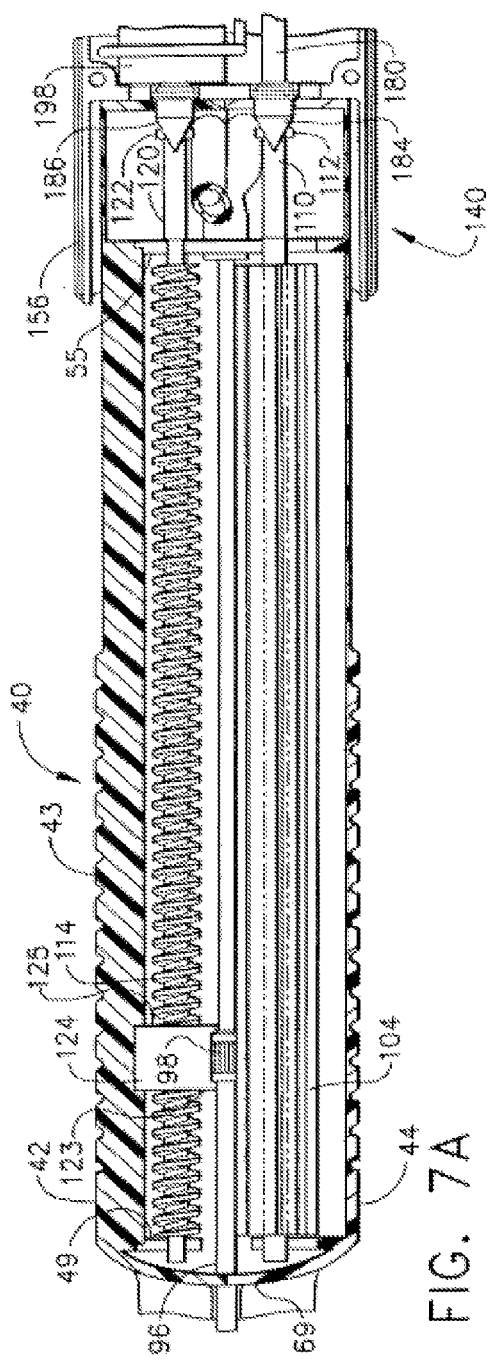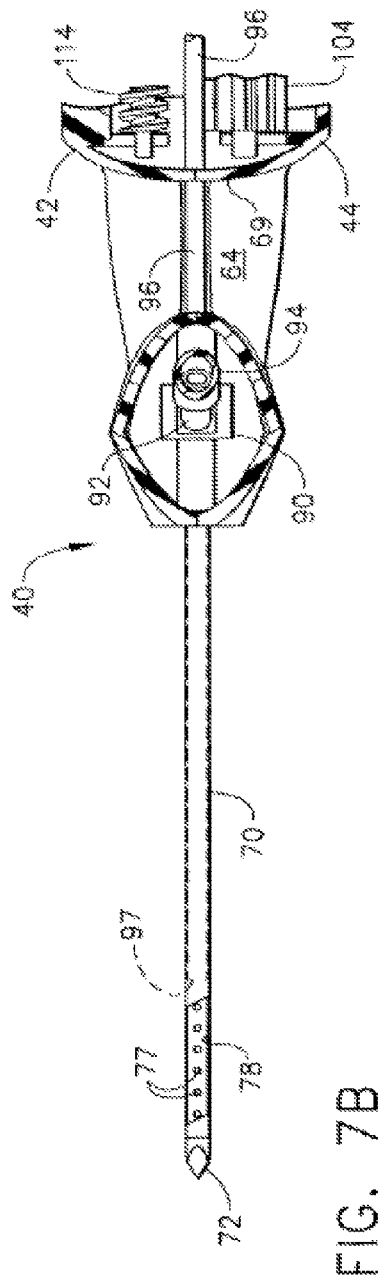
FIG. 7A
FIG. 7B

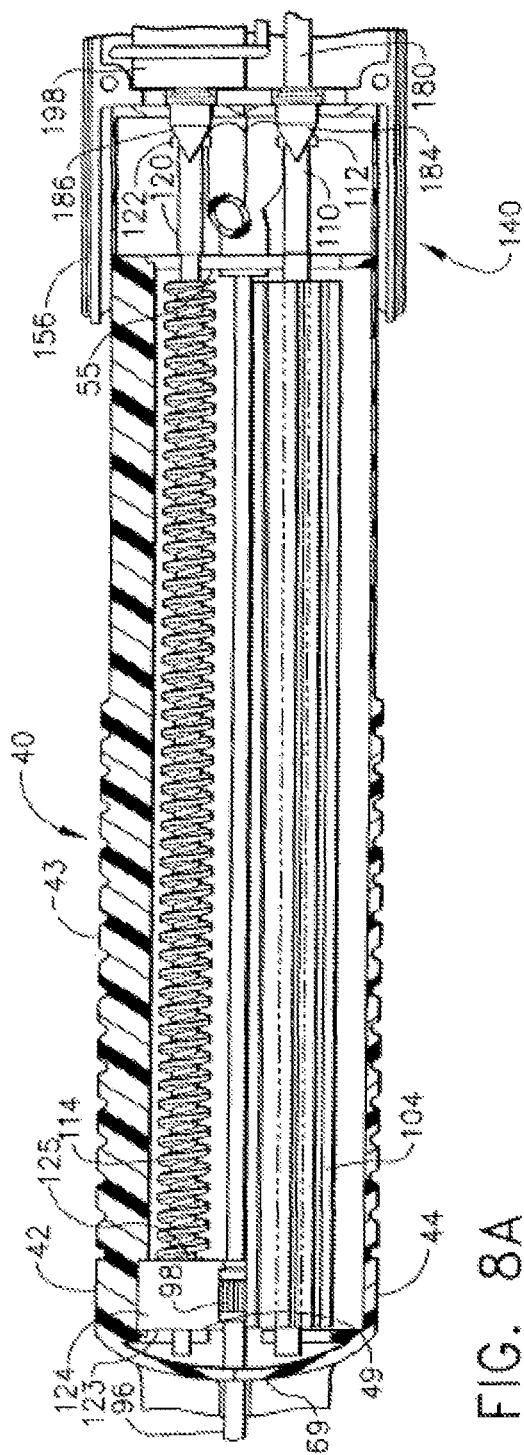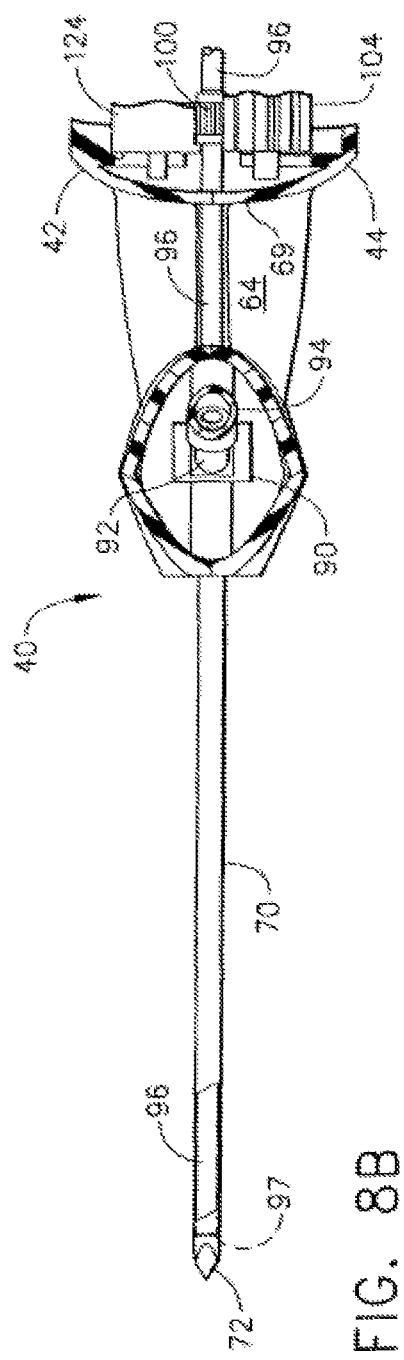
FIG. 8A
FIG. 8B

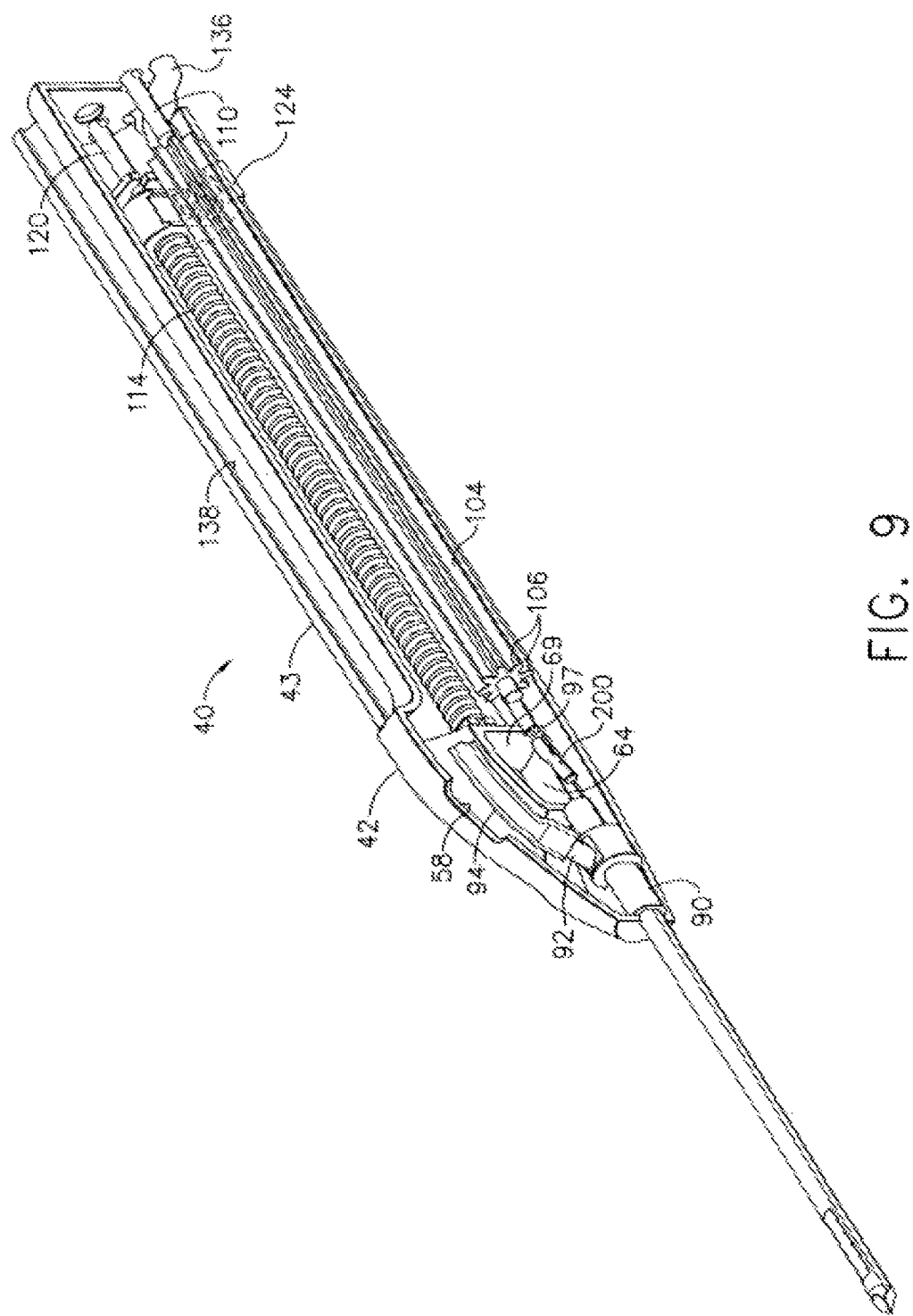

BIOPSY DEVICE

PRIORITY

This application is a divisional of U.S. Non-Provisional patent application Ser. No. 12/412,435, entitled "Biopsy Device," filed Mar. 27, 2009, the disclosure of which is incorporated by reference herein, which is a divisional of U.S. Pat. No. 7,510,534, entitled "Method For Operating Biopsy Device," filed May 2, 2003, the disclosure of which is incorporated by reference herein, and which is a divisional of U.S. Pat. No. 6,585,664, entitled "Calibration Method For An Automated Surgical Biopsy Device," filed Jul. 20, 2001, the disclosure of which is incorporated by reference herein.

FIELD OF THE INVENTION

The present invention relates, in general, to a method of calibrating a biopsy system and, more particularly, to a method of calibrating the translation and rotation of a cutter in a biopsy instrument. The method may further be used to determine the correct selection of probe size for the software installed in the control unit.

BACKGROUND OF THE INVENTION

The diagnosis and treatment of patients with cancerous tumors, pre-malignant conditions, and other disorders has long been an area of intense investigation. Non-invasive methods for examining tissue include palpation, X-ray, magnetic resonance imaging (MRI), computed tomography (CT), and ultrasound imaging. When a physician suspects that tissue may contain cancerous cells, a biopsy may be done using either an open procedure or a percutaneous procedure. For an open procedure, a scalpel is used to create a large incision in the tissue to provide direct viewing and access to the tissue mass of interest. The entire mass (excisional biopsy) or a part of the mass (incisional biopsy) may then be removed. In most percutaneous biopsy procedures, a needle-like instrument is inserted through a very small incision to access the tissue mass of interest and obtain a tissue sample for later examination and analysis.

Aspiration and core sampling are two percutaneous methods for obtaining a portion of tissue from within the body. In an aspiration procedure, tissue is fragmented into pieces and drawn through a fine needle in a fluid medium. The method is less intrusive than most other sampling techniques, however, it has limited application since the structure of tissue excised by aspiration is destroyed leaving only individual cells for analysis (cytology) and not the tissue structure for analysis (pathology). In core biopsy, a core or fragment of tissue is obtained in a manner, which preserves both the cells and the structure for histological examination. The type of biopsy used depends mainly on various factors, and no single procedure is ideal for all cases. Core biopsy, however, is very useful in a number of conditions and is widely used by physicians.

Examples of core sampling biopsy instruments are described in U.S. Pat. Nos. 5,562,822 and 5,769,086 (both issued to Ritchart, et al), and in U.S. Pat. No. 6,007,497 (issued to Huitema). Another example of a core sampling biopsy instrument is the biopsy instrument now marketed by Ethicon Endo-Surgery, Inc., Cincinnati, Ohio, under the trade name MAMMOTOME. Each of these instruments is a type of image-guided, percutaneous, coring, breast biopsy instrument, which uses a vacuum for retrieving tissue samples. A physician uses these instruments to capture "actively" (using the vacuum) tissue prior to severing it from the body. In particular, in these biopsy instruments, tissue is drawn into a port at the distal end of a piercing element, hereinafter referred to as a piercer. A cutting element, hereinafter referred to as a cutter, is rotated and advanced through a lumen of the piercer past the port. As the cutter advances through the port, it severs the tissue drawn into the port from the surrounding tissue. While the cutter is generally rotated using some type of motor, it may be advanced either manually or automatically. In the MAMMOTOME instrument, a disposable probe unit containing a piercer and cutter is first operationally connected to a reusable drive unit. The surgeon can then manually move the cutter back and forth by lateral movement of a knob mounted on the outside of the drive unit. Once the cutter is in place, proximal to the tissue port, further lateral movement of the knob is prevented and the cutter is advanced through the tissue port to sever tissue by twisting the knob. This arrangement is advantageous because the surgeon is able, through tactile and/or audible feedback, to determine whether the cutter is effectively cutting tissue or if there is a problem, such as binding, stalling, or an obstruction. The surgeon may then adjust the speed at which he moves the cutter through the tissue, stop the cutter or back the cutter away from the tissue. Since the surgeon can feel, through tactile feedback, at what point the cutter encounters an obstruction such as when it has reached its limits of linear travel, he will anticipate these obstructions and can readily control and stop the cutter at its most distal and proximal positions. Anticipating these obstructions and slowing or stopping the cutter translation just as the obstruction is reached thus avoids undo erratic movement of the instrument. Manual control of the cutter translation by the surgeon therefore allows the surgeon full control of the rate and distance of linear travel. Also, since each new disposable probe unit assembled to the reusable drive unit may vary in length slightly due to manufacturing tolerances, manual control by the surgeon allows for compensation for these size variations.

U.S. Pat. Nos. 5,562,822 and 5,769,086 describe automation of the translation of the cutter in a biopsy device to facilitate the procedure. However, if the procedure is automated as described in those references, the surgeon loses the benefit of the tactile feedback, which results when the cutter is advanced and retracted manually. It would therefore become necessary to require the cutter controlling means to know the precise condition, location, and travel distance of the cutter to ensure smooth and reliable operation of the biopsy system. In an automated biopsy system there may therefore be a need for the surgeon to follow a procedure to calibrate the cutter/probe unit prior to starting the surgical biopsy to ensure smooth and reliable operation. Such a calibration procedure would also be beneficial in confirming that the surgeon has selected the correctly sized biopsy probe for the software installed in the controlling means.

U.S. Pat. No. 6,086,544 (issued to Hibner, et al) describes a control apparatus for a surgical biopsy device. The biopsy device has a probe unit containing a rotatable, translatable cutter. The drive unit contains a cutter linear drive screw and cutter rotational drive screw. A control apparatus, containing drive motors, is connected to the drive unit through rotatable, flexible drive cables. A computing device is used to coordinate control of the rotation and linear translation of the cutter. This is accomplished by using optical sensors capable of providing very precise rotational position feedback information on the cutter linear drive screw and cutter rotational drive screw. Information supplied by these optical sensors to the computing device allows the computing device to control individual motors operating the drive cables connected to the cutter linear drive screw and cutter rotational drive screw. The computing device can therefore compare the actual performance of the biopsy device during the biopsy procedure to pre-established performance parameters and modify motor speeds to maintain system performance within pre-established parameters.

This system as disclosed however does not compensate for the aforementioned problem of the surgeon's lack of tactile feedback and control as the cutter reaches its limits of distal and proximal travel. This system reacts to the fact that the cutter's linear travel has reached its limit after the cutter has encountered a physical obstruction. Unfortunately the reaction time for the cable rotational sensors to detect the obstruction, send a message to the control apparatus, and the control apparatus terminate power to the cable drive motors may be too long to prevent the flexible, rotatable drive cables from twisting or "winding" do to the cutter's sudden and unexpected stop. If the user is not grasping the biopsy device tightly there is the risk the biopsy probe could inadvertently move and cause discomfort to the patent.

Another shortfall of this control system relates to its inability to compensate for different probe unit/drive unit combinations. Slight variations in cutter length, cutter position, or probe length occur due to manufacturing assembly procedures and tolerances. The manufacturer must accept certain manufacturing variations in order to make the device safe, functional, and affordable. Therefore, as a new probe unit is operationally connected to the reusable drive unit at the start of each biopsy procedure, the cutter linear travel distance and distal and proximal stopping points will be different from the preceding probe unit/drive unit combination. The probe manufacturer may also intentionally manufacture different "gauge" probes to different length specifications. The optical sensors could then be used to determine if the correctly sized probe is installed to match the software installed in the drive unit. Differently sized or "gauge" probes may therefore be manufactured to different length specifications so that, upon initial start-up, the clinician will be warned when an improper probe is installed for the software residing in the control unit.

Cutter rotational speed will also vary from one probe unit/drive unit combination to another due to manufacturing tolerances. It would, therefore, be advantageous to utilize the same optical sensors and computing device to establish the relative linear position and travel range of the cutter at initial start-up. They may also be used to establish whether or not excessive resistance is present within the cutter/probe unit that would cause the biopsy device to perform outside of the pre-established performance parameters, even before the biopsy device is put into actual clinical use.

What is therefore needed is a method in an automated core sampling biopsy device for determining the cutter's most distal and proximal linear travel position and providing feedback to the cutter control means for the purpose of establishing whether or not the cutter linear displacement is within a predetermined range before an actual biopsy procedure is performed. What is further needed is a method in an automated core sampling biopsy device for determining the rotational speed of the cutter and providing feedback to the cutter control means for the purpose of establishing whether or not the cutter rotational speed is within a predetermined range prior to a biopsy procedure.

SUMMARY OF THE INVENTION

The present invention is directed toward a method for calibrating a surgical biopsy system. The surgical biopsy system comprises a biopsy instrument and a control unit. The biopsy instrument comprises an elongated, hollow piercer, and a cutter rotatably and axially positionable relative to the piercer. A port is located in the piercer for receiving tissue samples. The surgical biopsy system comprises a control unit and a display for providing feedback signals to an operator.

A method according to the present invention includes the steps of: translating the cutter distally until the translation of the cutter is stopped at an extended position; recording the extended position; translating the cutter from the extended position proximally until the translation of the cutter is stopped at a retracted position proximal to the extended position; recording the retracted position. The method further comprises the step of rotating the cutter to a rotation speed while the cutter is located at the retracted position; determining if the rotation speed is within a predetermined rotation speed range; providing a feedback signal on the display allowing an operator to progress to the next procedural step when the rotation speed is within the predetermined rotation speed range.

A method is further disclosed for determining that the correctly sized biopsy instrument has been selected by an operator for a surgical biopsy system The surgical biopsy system comprises a biopsy instrument and a control unit. The biopsy instrument comprises an elongated, hollow piercer, a cutter rotatably and axially positionable relative to the piercer, and a port in the piercer for receiving tissue samples. The surgical biopsy system includes a control unit and a display for providing feedback signals to an operator.

A method according to the present invention includes the steps of: translating the cutter distally until translation of the cutter is stopped at an extended position; recording the extended position; translating the cutter from the extended position proximally until translation of the cutter is stopped at a retracted position proximal to the extended position; recording the retracted position; computing in the control unit total distance traveled between the retracted position and the extended position by the cutter; providing on the display a feedback signal to the operator when the total distance traveled falls outside a predetermined range.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

FIG. 6A is a top view in section of the probe assembly and a distal portion of the holster, revealing a cutter in a first, fully retracted position;

FIG. 6B is a top view in partial section of the distal end of the probe assembly illustrating the cutter in the first, fully retracted position wherein the port on the distal end of the piercer is open;

FIG. 7A is a top view in section of the probe assembly and a distal portion of the holster, revealing the cutter in the third position wherein the distal end of the cutter is immediately proximal to the port;

FIG. 7B is a top view in partial section of the distal end of the probe assembly with the port on the distal end of the piercer open and the distal end of the cutter in the third position immediately proximal to the port;

FIG. 8A is a top view in section of the probe assembly and a distal portion of the holster illustrating the cutter in the fourth, fully deployed position;

FIG. 8B is a top view in partial section of the distal end of the probe assembly illustrating the distal end of the cutter in the fourth position distal to the port at the distal end of the piercer;

FIG. 9 is an isometric view of the probe assembly with the left handle shell removed, showing the cutter in the first position, with a tissue sample shown deposited onto a tissue sampling surface;

DETAILED DESCRIPTION OF THE INVENTION

Figure 1:
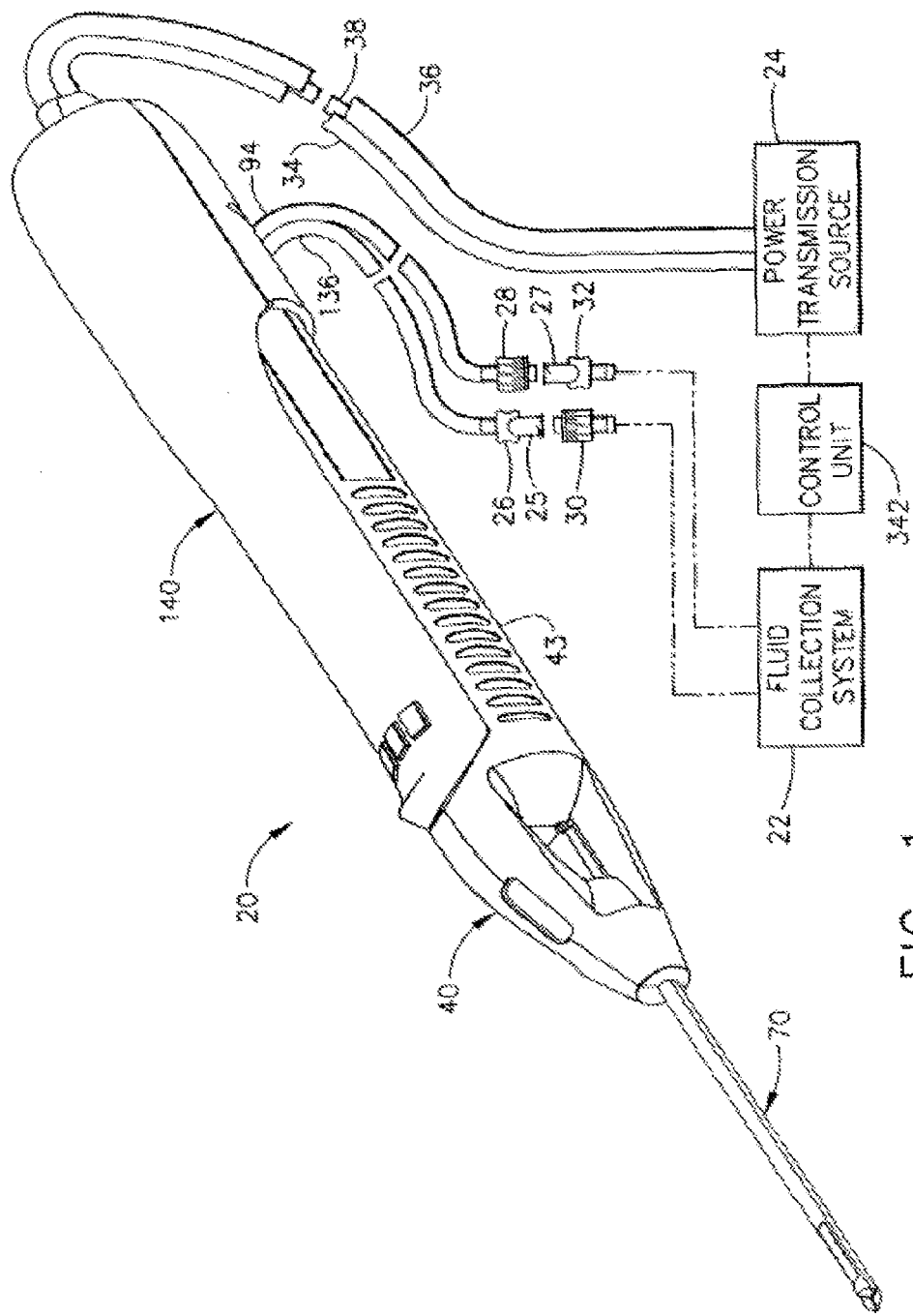
FIG. 1 is an isometric view of the present invention, a biopsy instrument, which includes a handpiece for the collection of soft tissue.

FIG. 1 shows a core sampling biopsy instrument comprising a probe assembly 40, a holster 140, a fluid collection system 22, a control unit 342, and a power transmission source 24. Probe assembly 40 is detachably connected to holster 140. Together they constitute a lightweight, ergonomically shaped, hand manipulatable portion referred to as a handpiece 20. Probe assembly 40 includes a piercer 70 extending distally from a hollow handle 43. Probe assembly 40 is fluidly connected to fluid collection system 22 by a first vacuum tube 94 and a second vacuum tube 136. First and second vacuum tubes are detachably connected to fluid collection system 22 by a first connector 27 and a second connector 25, respectively. First connector 27 has a male portion 32 and a female portion 28 attached to first vacuum tube 94. Second connector 25 has a female portion 30 and a male portion 26 attached to second vacuum tube 136. Connector portions, 26, 28, 30, and 32 are attached in this manner to prevent the accidental switching of first and second tubes, 136 and 94, to fluid collection system 22. Holster 140 includes a first rotatable shaft 34, a second rotatable shaft 36, and a control cord 38. First and second rotatable shafts, 34 and 36, are preferably flexible so that the operator may easily manipulate handpiece 20 with one hand. Control cord 38 operationally connects handpiece 20 to power transmission source 24 and control unit 342.

Since handpiece 20 is manipulated by the operator's hand rather than by an electro-mechanical arm, the operator may steer the tip of handpiece 20 with great freedom towards the tissue mass of interest. The surgeon has tactile feedback while doing so and can thus ascertain, to a significant degree, the density and hardness of the tissue being encountered. In addition, handpiece 20 may be held approximately parallel to the chest wall of the patient for obtaining tissue portions closer to the chest wall then may be obtained when using a instrument mounted to an electro-mechanical arm.

Those skilled in the art may appreciate that a mount or "nest" could be provided to hold handpiece 20 securely to the movable arm of an X-ray stereotactic table. This would provide the operator with the option to use handpiece 20 to access the tissue mass within the surgical patient in much the same manner as was described earlier for using the MAMMO-TOME instrument. This versatility may be advantageous to the operator, for example, in a situation where the handheld imaging device was temporarily not available for use, and it would be necessary to use the X-ray stereotactic table.

Figure 2:
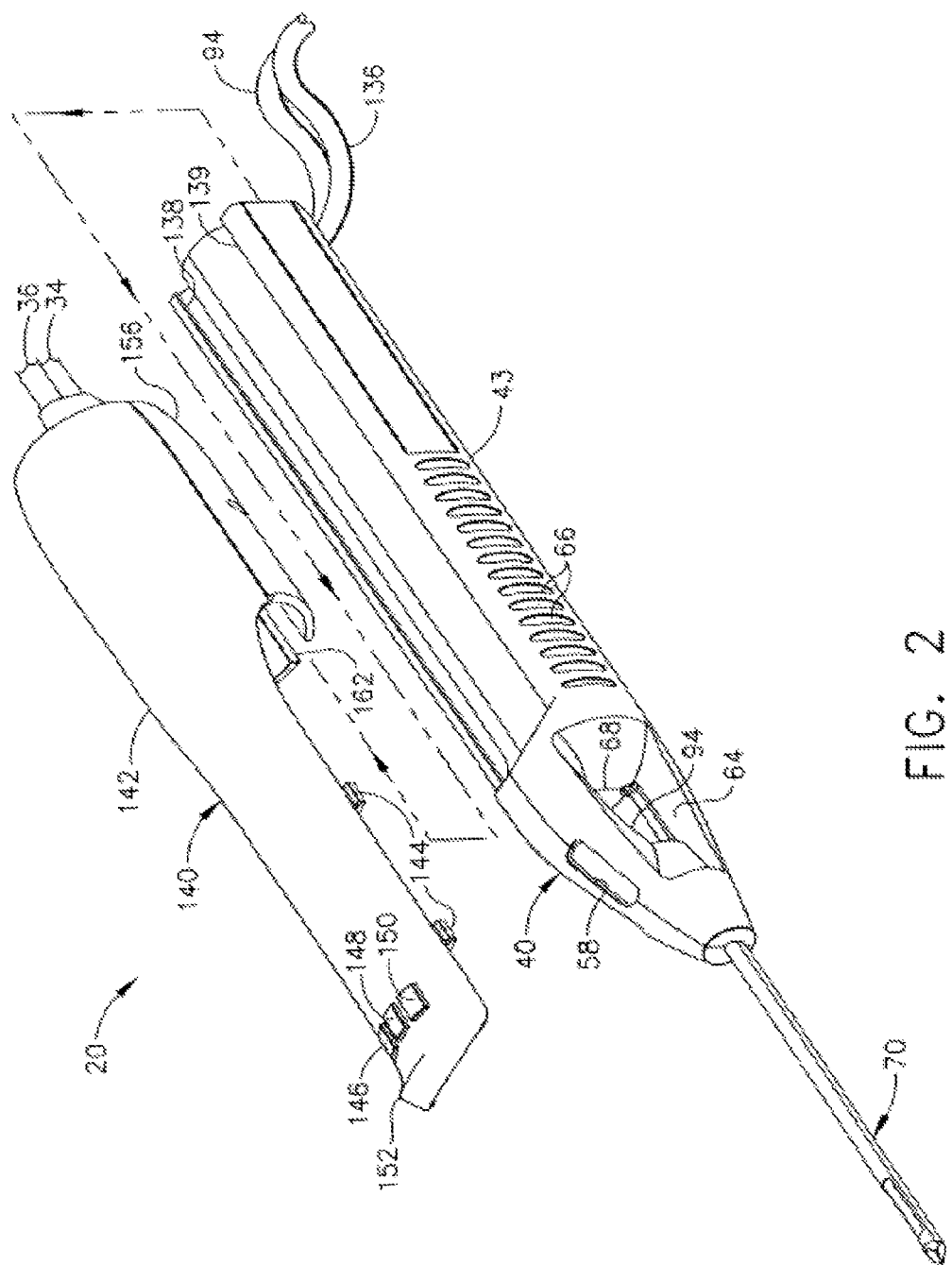
FIG. 2 is an isometric view of the handpiece showing a probe assembly prior to attachment to a holster.

FIG. 2 shows holster 140 and probe assembly 40 separated. A pair of tabs 144 project laterally from each side of a holster upper shell 142, and insert into right and left undercut ledges, 138 and 139 respectively, of hollow handle 43 of probe assembly 40. A plurality of indentations 66 is provided on handle 43 to improve the operator's grip on the instrument. A tube slot 162 in lower shell 156 of holster 140 provides clearance for first and second vacuum tubes, 94 and 136. A cutter forward switch 146 for moving a cutter 96 (see FIG. 3) in the distal direction, a cutter reverse switch 148 for moving cutter 96 in the proximal direction, and a vacuum switch 150, are mounted in the distal portion of holster 140 so that the operator can use handpiece 20 with a single hand. One-handed operation allows the other hand to be free, for example, to hold an ultrasonic imaging device. A ridge 152 on the distal end of holster 140 is provided to assist the operator in grasping handpiece 20 and in operating switches 146, 148, and 150.

Still in FIG. 2, probe assembly 40 includes a window 58 so that a portion of first vacuum tube 94 may be viewed. First and second vacuum tubes, 94 and 136, are made from a flexible, transparent or translucent material, such as silicone tubing. This enables visualization of the material flowing through the tubes, 94 and 136. By having window 58 in probe assembly 40, the operator can see the flow in first vacuum tube 94 without needing to look away from the tissue into which piercer 70 is inserted. A transverse opening 68 is provided in the distal end of hollow handle 43 which allows access from either side to a tissue sampling surface 64. The tissue extracted from the surgical patient is retrieved by the operator or by an assistant from tissue sampling surface 64.

Figure 3:
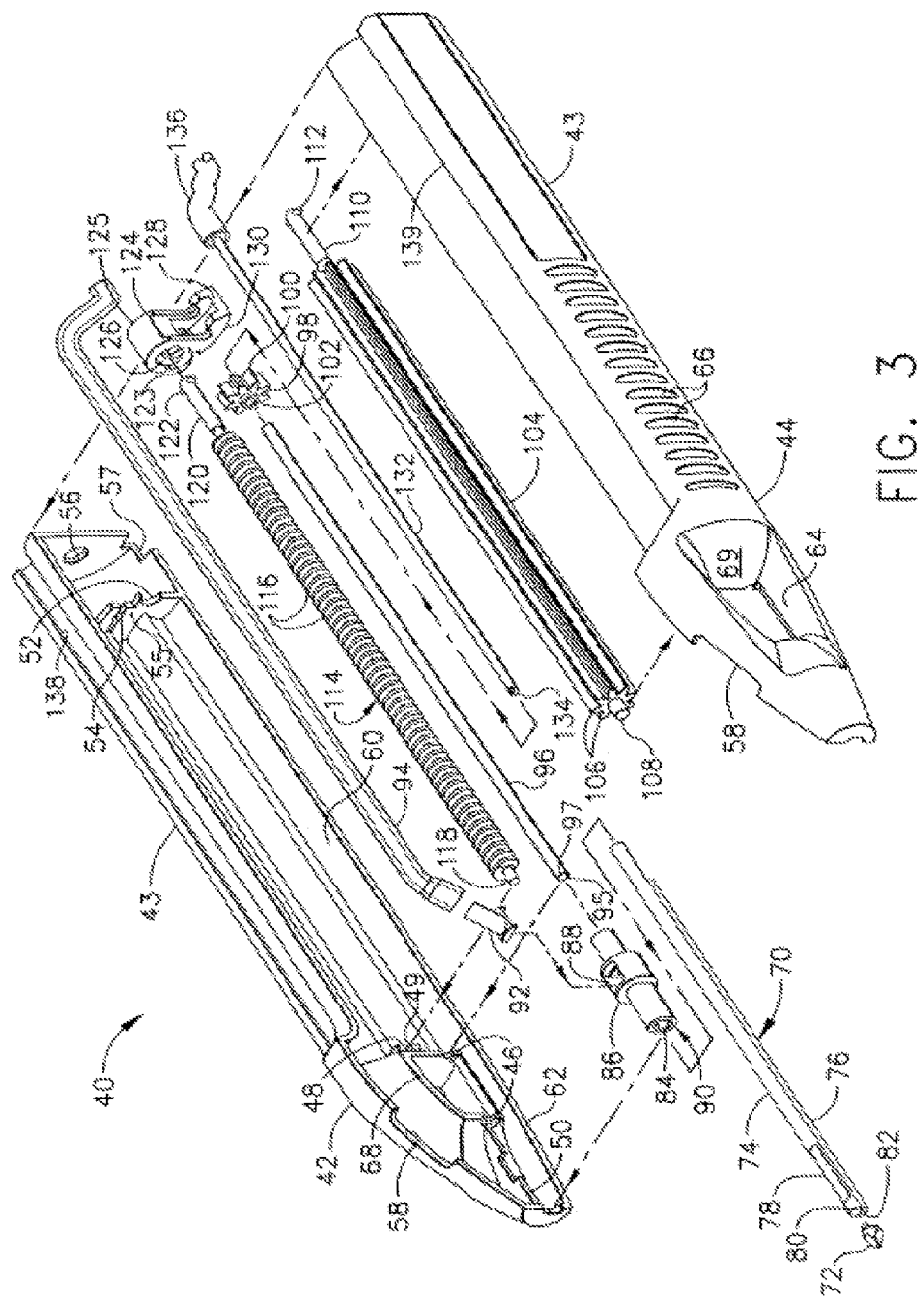
FIG. 3 is an exploded isometric view of the probe assembly illustrated in FIG. 2.

FIG. 3 is an exploded isometric view of probe assembly 40. Handle 43 is formed from a right handle shell 42 and a left handle shell 44, each injection molded from a rigid, biocompatible plastic such as polycarbonate. Upon final assembly of probe assembly 40, left and right handle shells, 42 and 44, are joined together by ultrasonic welding along a joining edge 62, or joined by any of several other methods well known in the art. Probe assembly 40 comprises piercer 70 having an elongated, metallic piercer tube 74 and a piercer lumen 80. On the side of the distal end of piercer tube 74 is a port 78 for receiving the tissue to be extracted from the surgical patient. Joined alongside piercer tube 74 is an elongated, tubular, metallic vacuum chamber tube 76 having a vacuum lumen 82. Piercer lumen 80 is in fluid communication with vacuum lumen 82 via a plurality of vacuum holes 77 (see FIG. 6B) located in the bottom of the "bowl" defined by port 78. These vacuum holes 77 are small enough to remove the fluids but not large enough to allow excised tissue portions to be removed through first vacuum tube 94 (see FIG. 2) which is fluidly connected to vacuum chamber 76. A metallic, sharpened distal end 72 is attached to the distal end of piercer 70. It is designed to penetrate soft tissue such as the breast of a female surgical patient. In this embodiment, sharpened distal end 72 is a three-sided, pyramidal-shaped point, although the tip configuration may also have other shapes.

Still referring to FIG. 3, the proximal end of piercer 70 is attached to a union sleeve 90 having a longitudinal bore 84 through it, a widened center portion 86, and a transverse opening 88 through widened center portion 86. Union sleeve 90 is mounted between left and right handle shells, 44 and 42 respectively, on a pair of union sleeve ribs 50 (only the rib in the right handle shell is visible) projecting from each handle shell. An elongated, metallic, tubular cutter 96 is axially aligned within longitudinal bore 84 of union sleeve 90 and piercer lumen 80 of piercer 70 so that cutter 96 may slide easily in both the distal and proximal directions. A pair of cutter guides 46 are integrally molded into each of handle halves, 42 and 44, to slidably retain cutter 96 in an co-axially aligned position with the proximal end of piercer tube 74. Cutter 96 has a cutter lumen 95 through the entire length of cutter 96. The distal end of cutter 96 is sharpened to form a cutter blade 97 for cutting tissue held against cutter blade 97 as cutter 96 is rotated. The proximal end of cutter 96 is attached to the inside of a cutter gear bore 102 of a cutter gear 98. Cutter gear 98 may be metallic or polymeric, and has a plurality of cutter gear teeth 100, each tooth having a typical spur gear tooth configuration as is well known in the art.

Still in FIG. 3, cutter gear 98 is driven by an elongated drive gear 104 having a plurality of drive gear teeth 106 designed to mesh with cutter gear teeth 100. The function of drive gear 104 is to rotate cutter gear 98 and cutter 96 as they translate in both longitudinal directions. Drive gear 104 is preferably made from a metal such as stainless steel. A distal drive axle 108 projects from the distal end of drive gear 104 and mounts into an axle support rib (not visible) molded on the inside of left handle shell 44. A gear shaft 110 projects from the proximal end of drive gear 104 and is supported by a gear shaft support rib (not visible) also molded on the inside of left handle shell 44. A left cross pin 112 is attached to the proximal end of gear shaft 110 as a means for rotationally engaging drive gear 104.

Still referring to FIG. 3, a carriage 124 is provided to hold cutter gear 98 and to carry cutter gear 98 as it is rotated in the distal and proximal directions. Carriage 124 is preferably molded from a rigid polymer and is cylindrically shaped with a threaded bore 126 through it and with a carriage foot 130 extending from its side. Carriage 124 contains a distal carriage wall 123 and proximal carriage wall 125, each located on opposite faces of carriage 124 and oriented at approximately ninety degrees to the axis of threaded bore 126. Carriage foot 130 has a recess 128 formed into it for rotatably holding cutter gear 98 in the proper orientation for cutter gear teeth 100 to mesh properly with drive gear teeth 106. Carriage 124 is attached via threaded bore 126 to an elongated screw 114, which is parallel to drive gear 104. Screw 114 has a plurality of conventional lead screw threads 116 and is preferably made from a stainless steel. The rotation of screw 114 in one direction causes carriage 124 to move distally, while the reverse rotation of screw 114 causes carriage 124 to move proximally. In turn cutter gear 98 moves distally and proximally according to the direction of the screw rotation, and cutter 96 is advanced or retracted. In this embodiment, screw 114 is shown with a right hand thread so that clockwise rotation (looking from the proximal to distal direction) causes carriage 124 to translate in the proximal direction. It is also possible to use a left-hand thread for screw 114 as long as provisions are made to do so in control unit 342. A distal screw axle 118 and a proximal screw shaft 120 project from the distal and proximal ends, respectively, of screw 114. Distal screw axle mounts rotatably in a distal screw support 48 of right handle shell 42 while proximal screw shaft 120 mounts rotatably in a proximal screw support 54, also in right handle shell 42. Distal screw support 48 contains distal screw support wall 49, which is parallel to distal carriage wall 123. Proximal screw support 54 contains proximal screw support wall 55, which is parallel to proximal carriage wall 125. A right cross pin 122 is attached to the proximal end of screw shaft 120 as a rotational engagement means.

Figure 4:
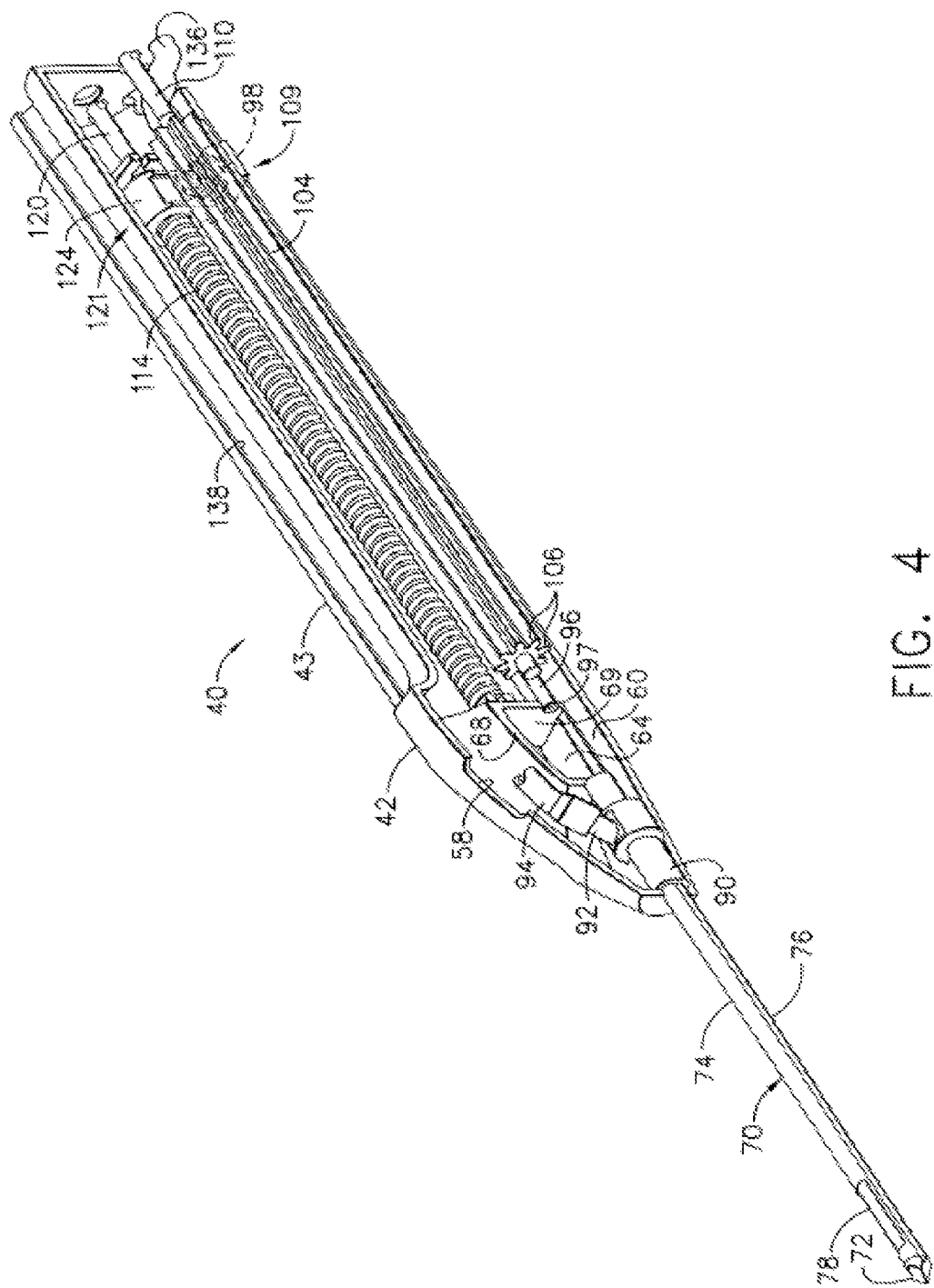
FIG. 4 is an isometric view of the probe assembly of FIG. 2 with the left handle shell removed to reveal the internal components.

At this point in the detailed description, it is important to point out that during operation of the present invention, cutter 96 translates in either direction between a fully retracted position just proximal to tissue sampling surface 64 and a fully deployed position just distal to port 78 (see FIG. 4). There are key intermediate positions along the length (about six inches for this particular embodiment) of the cutter translation. When the distal end of cutter 96 reaches each of these positions, important adjustments to either the cutter rotational speed (sometimes referred to simply as rotation speed) or the cutter translational speed (sometimes referred to simply as translation speed), or both, are made automatically. For the embodiment of the biopsy device described herein, there are four positions along the length of the cutter translation. At these positions, signals to control unit 342 are sent in order to make appropriate adjustments to cutter rotational speed and/or cutter translational speed. To facilitate description of the cutter positions, they are to be understood as actually the positions of cutter blade 97 on the distal end of cutter 96. These four cutter positions are the following: a first position where cutter 96 is just proximal to the tissue sampling surface 64 (see FIG. 6B); a second position where cutter 96 is just distal to tissue sampling surface 64 (in FIG. 6B, cutter blade 97 would be located to the left of tissue sampling surface 64 instead of to the right); a third position where cutter 96 is just proximal to port 78 (see FIG. 7B); and a fourth position where cutter 96 is just distal to port 78 (see FIG. 8B). These four cutter positions are given by way of example although numerous other cutter positions may be used in the present invention for automatically signaling adjustments to cutter rotational speed and/or translational speed. These four positions are sometimes referred to as a position one, a position two, a position three, and a position four. They are also referred to as a position 1, a position 2, a position 3, and a position 4.

Probe assembly 40 is detachably connected to holster 140. Probe assembly 40 and holster 140 are separable so that, in the case of the probe being manufactured as a reusable structure, the entire probe assembly 40 may be disassembled, cleaned, reassembled, and sterilized prior to reuse. In the case of the probe being manufactured as disposable, the entire probe assembly 40 may be properly disposed of. The fact that these two components are separable requires that a calibration procedure be performed each time a probe assembly 40 and holster 140 are mated.

Figure 3A:
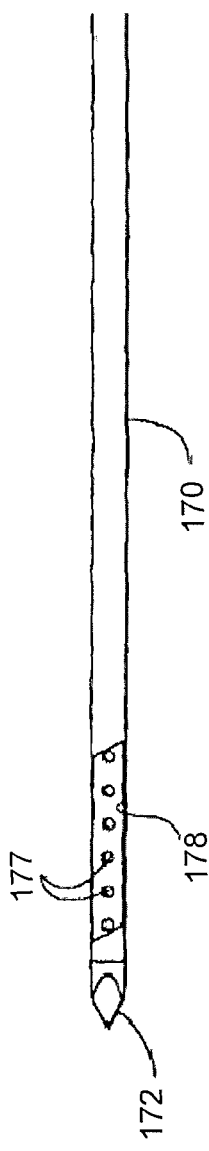
FIG. 3A is a top view of another exemplary piercer for use with the probe assembly of FIG. 3.
Figure 3B:
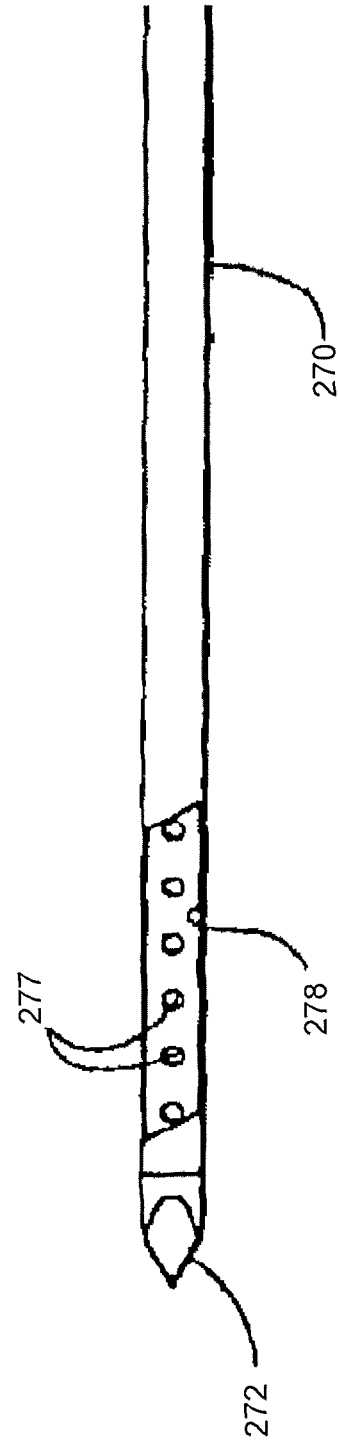
FIG. 3B is a top view of another exemplary piercer for use with the probe assembly of FIG. 3.

It should be noted here that different diameter or "gauge" probes may be intentionally manufactured to different lengths, as shown in FIGS. 3A and 3B. By specifying a specific length for piercer 70, a unique cutter translation distance may be programmed into control unit 342 software for specific probe gauges. This will aid in identifying, at start-up, that the proper probe has been selected for the software loaded in the control unit, as will be described in more detail later.

Alternately, the pitch of screw threads 116 on screw 114 may be specified differently for different gauge probes. The translation distance for cutter 96 is determined in control unit 342, as is described in more detail later, by counting the number of revolutions of screw 114. As the pitch of screw threads 116 is increased or decreased, the linear distance traveled by cutter 96 is increased or decreased per each revolution of screw 114. Different pitch threads specific to probe gauge can therefore be used to effect cutter translation distance. This information is communicated to control unit 342 and can be used to determine if the correct gauge probe is selected for the software loaded in control unit 342, as will be described in more detail later.

Now referring again to FIG. 3, the distal end of first vacuum tube 94 is attached to a polymeric vacuum fitting 92 which inserts tightly into transverse opening 88 of union sleeve 90. This allows the communication of fluids in piercer lumen 80 to fluid collection system 22. First vacuum tube 94 is contained within hollow handle 43 in an open space above screw 114 and drive gear 104, and exits the distal end of hollow handle 143 through an opening 57. Second vacuum tube 136 is fluidly attached to the proximal end of an elongated, metallic, tubular tissue remover 132. Second vacuum tube 136 exits hollow handle 43 alongside first vacuum tube 94 out the opening 57. A strainer 134 is attached to the distal end of tissue remover 132 to prevent the passage of fragmented tissue portions through it and into fluid collection system 22. Tissue remover 132 inserts slidably into tubular cutter 96. During operation of the biopsy instrument, tissue remover 132 is always stationary and is mounted between a pair of proximal supports 52 on the inside of the right and left handle shells, 42 and 44 respectively. When cutter 96 is fully retracted to the first position, the distal end of tissue remover 132 is approximately even with the distal end of cutter 96. The distal end of cutter 96 when at its first, fully retracted position, is slightly distal to a vertical wall 69 which is proximal and perpendicular to tissue sampling surface 64.

In FIG. 3, a right access hole 56 is shown in the proximal end of right handle shell 43. Right access hole 56 provides access to the proximal end of screw 114 for operational engagement to power transmission source 24. Similarly, a left access hole (not shown) is provided in left handle shell 44 to provide access to the proximal end of drive gear 104 for operational engagement with power transmission source 24.

Tissue remover 132 has two functions. First, it helps to evacuate fluids contained in piercer lumen 80. This is accomplished by the attachment of second vacuum tube 136 to the proximal end of tissue remover 132. Since the distal end of tissue remover 132 is inserted into piercer lumen 80, piercer lumen 80 is fluidly connected to fluid collection system 22. Second, tissue remover 132 removes tissue from cutter 96 as follows. When a tissue sample is taken, cutter 96 advances to the fourth position just distal to port 78, and a severed tissue sample 200 (see FIG. 9) is captured within cutter lumen 95 in the distal end of cutter 96. Then cutter 96 translates to the first position so that cutter blade 97 is just distal to tissue sampling surface 64. At this position of cutter 96, the distal end of tissue remover 132 (which is always stationary) is approximately even with the distal end of cutter 96. Therefore, any tissue portion of significant size contained within cutter lumen 95 is pushed out of cutter lumen 95 and onto tissue sampling surface 64, as is shown in FIG. 9. The operator or an assistant may then retrieve tissue sample 200.

Now turning to FIG. 4, an isometric view of probe assembly 40 with left handle shell 44 removed reveals the placement of the components described for FIG. 3. Part of first vacuum tube 94 has also been removed for clarity. Carriage 124 is shown in the fully retracted position so that cutter 96 is also at the fully retracted or first position. Cutter blade 97 is slightly distal to vertical wall 69 on handle 43. Carriage foot 130 of carriage 124 is adapted to slide along a carriage guide surface 60 on the inside bottom of hollow handle 43.

As shown in FIG. 4, a cutter translational transmission 121 includes carriage 124, screw 114, and screw shaft 120. A cutter rotational transmission 109 includes drive gear 104, cutter gear 98, and gear shaft 110.

Figure 5:
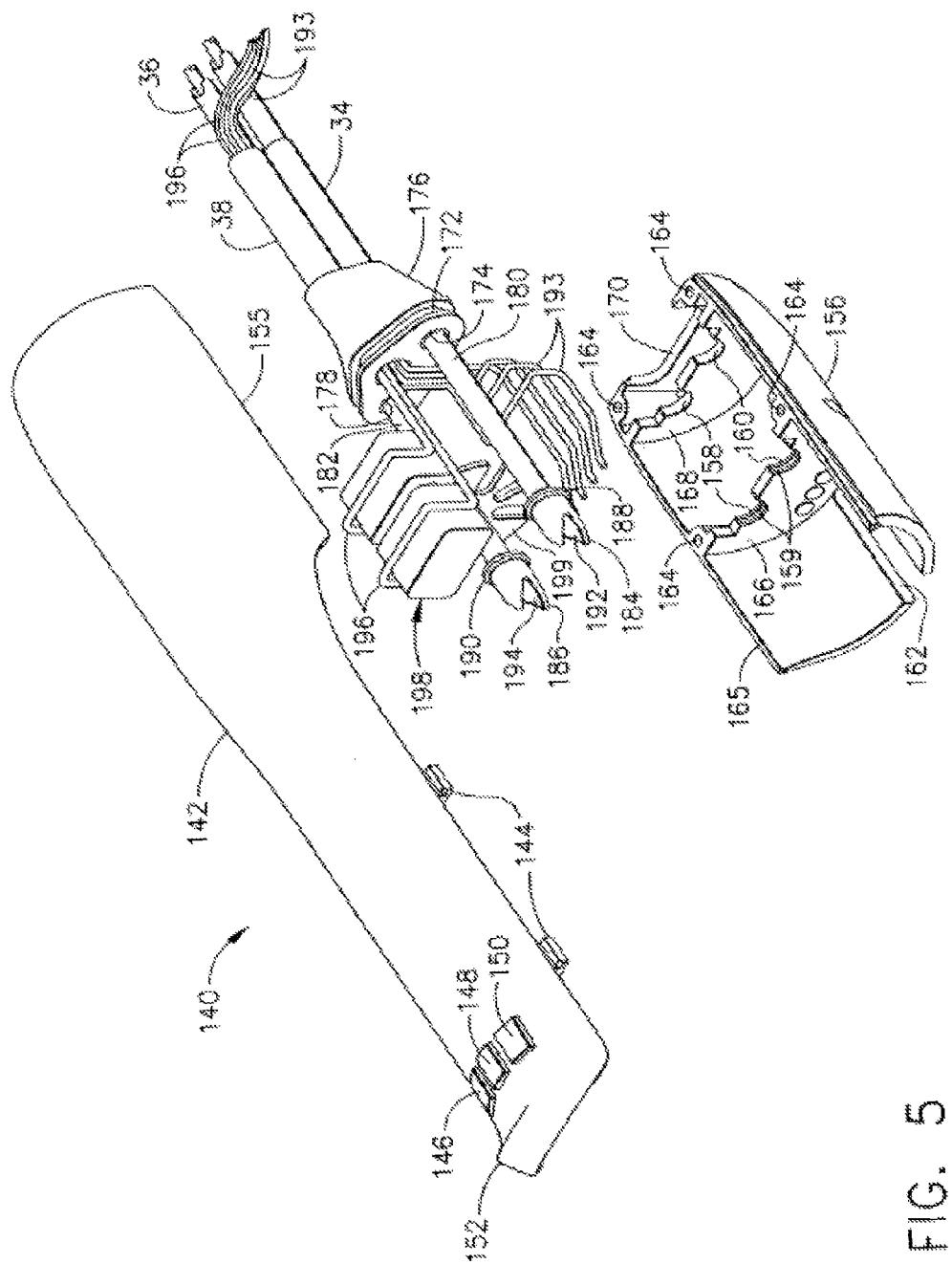
FIG. 5 is an exploded isometric view of the holster illustrating a non-encased rotation sensor mounted on a screw drive shaft.

FIG. 5 is an exploded isometric view of holster 140. A holster upper shell 142 and a holster lower shell 156 are each injection molded from a rigid, biocompatible plastic such as polycarbonate. Upon final assembly, the shells are joined together by screws (not shown) or other types of fasteners well known in the art, into a plurality of alignment holes 164. A gear drive shaft 180 and a screw drive shaft 182 are contained within the proximal, enclosed portion of holster 140. These shafts extend from a grommet 176 which has a groove 172 for retainably mounting onto shell edge 170 of both holster upper and lower shells, 142 and 156, respectively. Grommet 176 rotatably attaches first rotatable shaft 34 to screw drive shaft 182 and second rotatable shaft 36 to gear drive shaft 180. First rotatable shaft 34 rotatably inserts into a left bore 172 of grommet 176. Second rotatable shaft 36 rotatably inserts into a right bore 178. Grommet 176 also provides a strain-relieved attachment of control cord 38 to holster 140.

Still referring to FIG. 5, gear drive shaft 180 is supported rotatably upon a pair of gear drive mounts 160 formed into a first wall 166 and a second wall 168 of the inside of holster shells, 142 and 156. Screw drive shaft 182 is likewise supported rotatably on screw drive mounts 158. A left coupler 184 is attached to the distal end of drive gear shaft 180 and has a left coupler mouth 192 for rotational engagement with left cross pin 112 attached to gear shaft 110. When probe assembly 40 shown in FIG. 4 is attached to holster 140, gear shaft 110 becomes rotatably engaged to gear drive shaft 180. This may be seen more clearly in FIG. 6A. Similarly, screw drive shaft 182 has a right coupler 186 with a mouth 194, which rotatably engages with cross pin 122 of screw shaft 120. Each of the left and right couplers, 184 and 186, have a coupler flange, 188 and 190, which rotatably insert into thrust slots 159 formed into the corresponding portions of drive mounts 158 and 160. Coupler flanges, 188 and 190, bear the translational loading of drive shafts, 180 and 182.

Still referring to FIG. 5, holster 140 further includes an non-encased, rotation sensor 198 for providing an electronic signal to control unit 342 to be described later. A suitable example of an non-encased rotation sensor 198 is an optical encoder, Part Number HEDR-81002P, available from the Hewlett-Packard Corporation. In this first embodiment, non-encased rotation sensor 198 is mounted within the inside of holster upper shell 142 and in a position directly above screw drive shaft 182. A fluted wheel 199 is attached to screw drive shaft 182 and extends in front of a light emitting diode contained within non-encased rotation sensor 198. As fluted wheel 192 rotates, the interrupted light beams are electronically detected and transmitted back to control unit 342 to provide information about the rotational speed of screw drive shaft 182. By counting the number of screw rotations from the beginning of operation, the instantaneous axial translation position and speed in either direction of cutter 96 may be calculated by control unit 342. Non-encased rotation sensor leads 196 pass through grommet 176 and are part of the bundle of conductors within control cord 38.

Holster 140 shown in FIG. 5 has forward, reverse, and vacuum switches, 146, 148, and 150 respectively, mounted on the inside of holster upper shell 142. Switches 146, 148, and 150 are electronically connected to a plurality of conductors 193 contained in control cord 38. Vacuum switch 150 operates fluid communication with fluid collection system 22 and also sets control unit 342 to respond to various commands as described later. Reverse switch 148 operates the movement of cutter 96 in the proximal direction and sets control unit 342 to respond to various commands. Forward switch 150 operates the movement of cutter 96 in the distal direction and sets control unit 342 to respond to various commands. The physical locations of switches, 146, 148, and 150 on handpiece 20 are not restricted to the locations depicted in FIG. 2. Other embodiments of handpiece 20 of the present invention may incorporate certain ergonomic or other considerations, and switches 146, 148, and 150 may be located elsewhere. In addition, switches 146, 148, and 150 may be of varying shapes and colors, or have varying surface treatments, so as to distinguish from one another, and to assist the operator in differentiating each one from the others either by tactile or visual identification.

As already described, FIGS. 6A through 8A depict three of the four positions of cutter 96 during the operation of the present invention as embodied in the prior FIGS. 1-5. The three positions are most easily distinguished by observing the relative positions of carriage 124 (which moves together with cutter 96) and cutter blade 97 on the distal end of cutter 96.

In FIGS. 6A and 6B, cutter 96 is at the first position. Carriage 124 begins its translation on the proximal ends of drive gear 104 and screw 114. Cutter blade 97 is shown to be immediately proximal to tissue sampling surface 64. In the first position, tissue sample 200 may be retrieved from tissue-sampling surface 64 (see FIG. 9).

In FIGS. 7A and 7B, cutter 96 is at the third position. Carriage 124 is shown to have translated to the intermediate position that is a short distance from the distal ends of screw 114 and drive gear 104. Cutter blade 97 is shown by hidden lines to be located just proximal to port 78. Vacuum holes 77 are open to port 78 so that soft tissue adjacent to port 78 can be pulled into port 78 when first vacuum tube 94 is fluidly connected to the vacuum of fluid collection system 22.

FIGS. 8A and 8B show cutter 96 at the fourth position. Carriage 124 is located near the distal ends of screw 114 and drive gear 104. Cutter blade 97 is shown now (by hidden lines) to be distal to port 78 and to be covering vacuum holes 77. The tissue pulled into port 78 will have been severed by the rotating, advancing cutter blade 97 and stored inside cutter lumen 95 of the distal end of cutter 96. When cutter 96 retracts back to the first position as shown in FIGS. 6A and 6B, tissue sample 200 may be retrieved as shown in FIG. 9.

Figure 10:
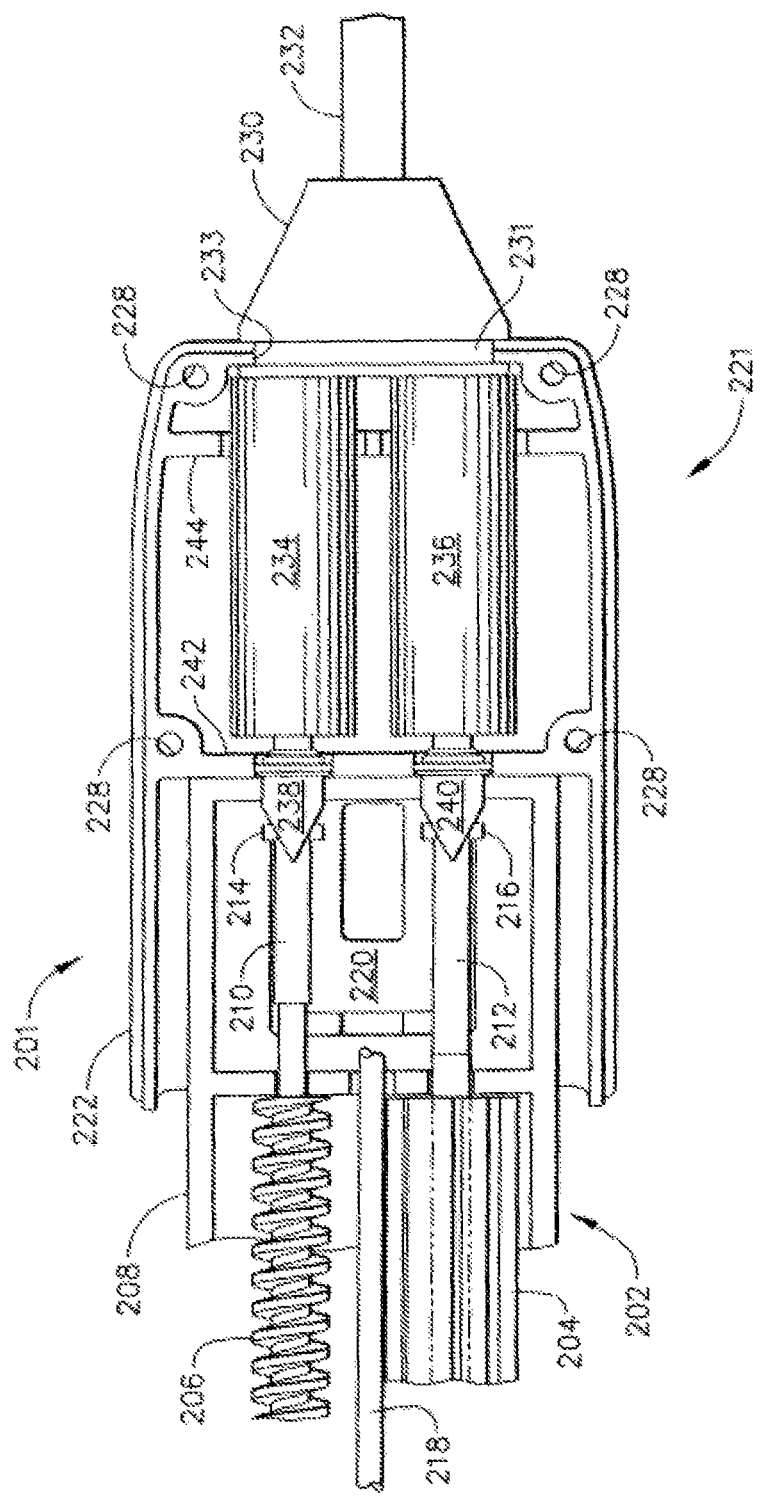
FIG. 10 is a partial top view of a further embodiment of the present invention wherein a first and a second motor are contained within a handheld holster rather than in a remotely located control unit as for the embodiment of FIG. 5, and wherein the holster upper shell and the probe assembly upper shell have been removed to reveal the internal components.

FIG. 10 shows a further embodiment of the present invention, including an integrally motorized holster 221. The main difference from the embodiment of holster 140 shown in FIG. 5 is that integrally motorized holster 221 contains a first brushless, electric motor 234 and a second, brushless electric motor 236. A suitable example for first and second brushless, electric motors, 234 and 236, is Part Number B0508-050, available from Harowe Servo Controllers, Incorporated. In the embodiment of FIG. 10, rotatable shafts 34 and 36 have been eliminated so that only a control/electrical power cord 232 is required to electrically connect integrally motorized holster 221 to power transmission source 24 and control unit 342 (see FIG. 1). A holster lower shell 222 has a first wall 242 and a second wall 244, which are spaced apart and adapted to support the pair of brushless, electric motors, 234 and 236, in a side-by-side arrangement. The use of brushless, electric motors, 234 and 236, eliminates the need for a separate rotation sensor to be mounted in the drive train of one or both of a screw 206 and a drive gear 204 as was described for holster 140 shown in FIG. 5. As for holster 140 of FIG. 5, when a probe assembly 202 is attached to integrally motorized holster 221, a right coupler 238 rotationally engages a right cross pin 214 of a screw shaft 210. A left coupler 240 rotationally engages a left cross pin 216 of a gear shaft 212. An attachment slot 233 in holster shell 222 retains a grommet 230 having a grommet groove 231. Fastener holes 228 are provided to fasten holster lower shell 222 to a holster upper shell (not shown) using screws or other types of fasteners well known in the art.

Another difference of integrally motorized holster 221 shown in FIG. 10 from holster 140 shown in FIG. 5 is that probe assembly 202 comprises a lower shell 208 and an upper shell (not shown). Hollow handle 43 of holster 140 shown in FIG. 5, however, is divided vertically into left and right shells, 44 and 42 respectively. This arrangement facilitates the mounting of brushless motors, 234 and 236, and additional features described next.

Figure 11:
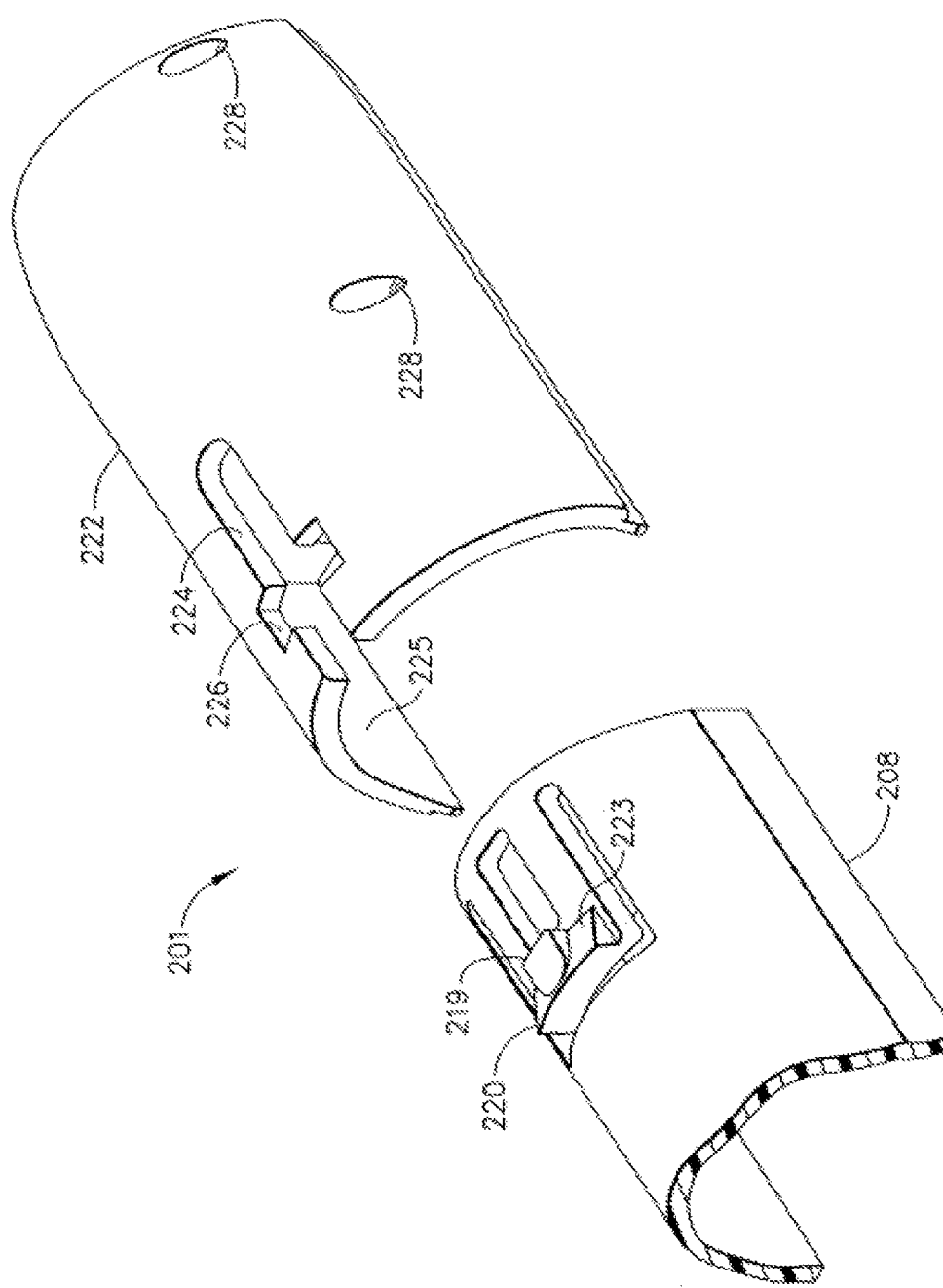
FIG. 11 is an isometric view of the holster and probe assembly lower shells shown in FIG. 10, wherein the holster lower shell includes a slot for the removable attachment to a latch on the probe assembly lower shell.
Figure 12:
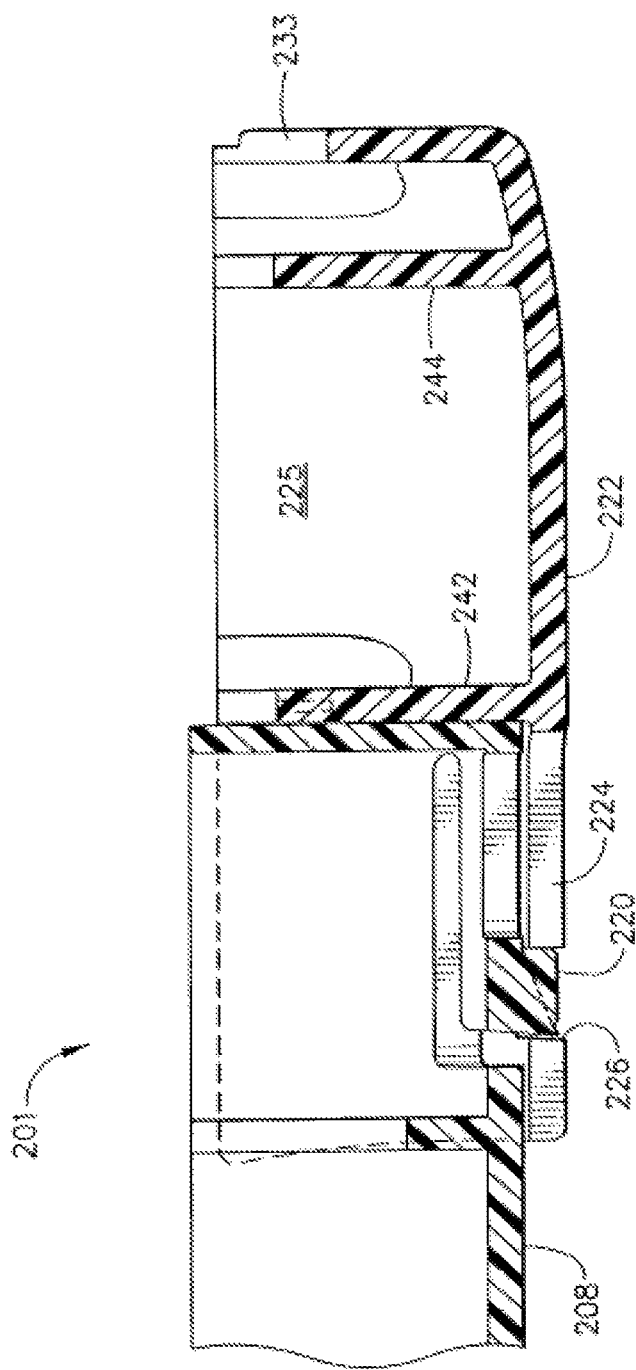
FIG. 12 is a longitudinal section of the holster and probe assembly lower shells of FIG. 11, illustrating their removable attachment to each other.

FIG. 11 shows an isometric view of probe lower shell 208 and holster lower shell 222 of integrally motorized holster 221 illustrated in FIG. 10. The view in FIG. 11 is upside-down with respect to the view in FIG. 10 in order to show a probe latch 220 molded into probe lower shell 208. Probe latch 220 is a cantilever beam and can be deflected downwards by a force applied to a latch ramp surface 223. Probe latch 220 further comprises a latch projection 219 for insertion into a holster slot 224 as probe assembly 202 is inserted into integrally motorized holster 221. Ramp surface 223 is deflected downwards by interaction with an inside surface 225 of holster shell 222 and retainably snaps into a slot key 226 when probe assembly 202 is fully inserted into integrally motorized holster 221. By engaging probe latch 220 in this way, the left and right couplers, 240 and 238, rotationally engage to drive shaft 212 and gear shaft 210, respectively, as shown in FIG. 10. To remove probe assembly 202 from integrally motorized hoister 221, the operator presses on projection 219 while pulling them apart. FIG. 12 shows a longitudinal section through the center axis of probe lower shell 208 and holster lower shell 222 of FIG. 11 for when they are fully attached together.

Figure 13:
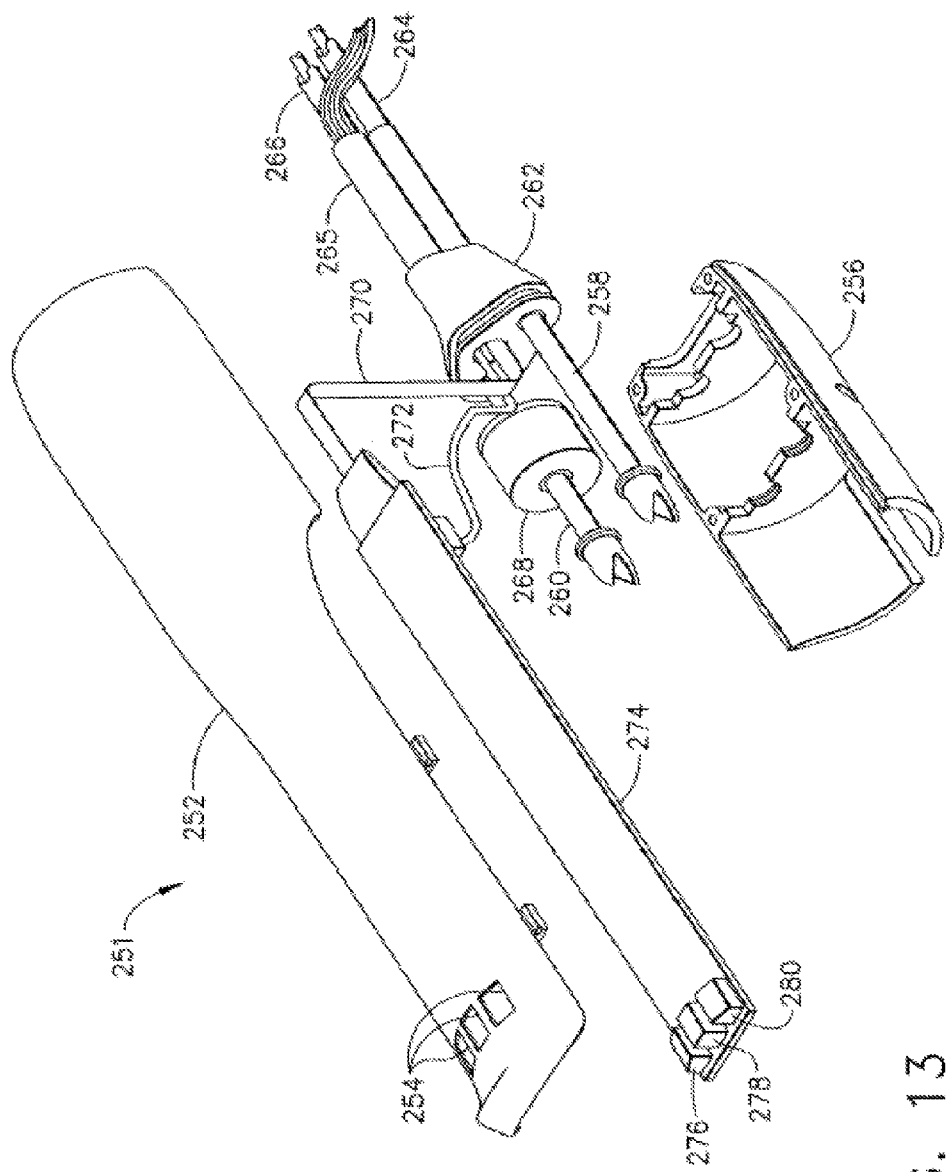
FIG. 13 is an exploded isometric view of a further embodiment of the holster illustrated in FIG. 5, wherein the further embodiment includes the three switches being mounted on a switch board electrically connected by a ribbon cable to the control cord (instead of the three switches being electrically connected to the control cord by discrete switch conductors as illustrated in FIG. 5), and wherein the further embodiment includes an encased rotation sensor rather than the non-encased rotation sensor of the embodiment illustrated in FIG. 5.

FIG. 13 is an exploded isometric view of a further embodiment of the present invention that includes a switchboard 274 integrally mounted inside of a switch board-modified holster 251. Switch board-modified holster 251 may be used with probe assembly 40 shown in FIGS. 1-4. A first rotatable shaft 264 and a second rotatable shaft 266 are each attached by a grommet 262 to a drive shaft 258 and a screw shaft 260, respectively. Rotatable shafts, 264 and 266, are preferably flexible too, in order for switch board-modified holster 251, together with probe assembly 40 (see FIG. 2), to be easily manipulatable with one hand. An encased rotation sensor 268 (also referred to as a third sensor) is shown mounted on a screw shaft 260. A suitable example for encased rotation sensor 268 is a miniature optical encoder, which is commercially available as Model Number SEH17 from CUI Stack, Incorporated. It is electrically connected to a switchboard 274 which mounts to the inside of holster upper shell 252. Switchboard 274 also has a ribbon cable 270 containing a plurality of conductors for conveying electronic information to and from control unit 342. Switch board 274 has mounted on its distal end, three switches, 276, 278, and 280, for operation of the present invention in the same manner as described for holster 140 of FIG. 5: a vacuum switch 280 for fluidic connection to the vacuum of fluid collection system 22; a forward switch 276 for the forward movement of cutter 96; and a reverse switch 278 for the reverse movement of cutter 96. Switches 276, 278 and 280 project through three switch openings 254 of holster upper shell 252. A holster lower shell 256 attaches to upper shell 252 as in the other embodiments to enclose the components of the proximal portion of holster 251. It is well known in the art that controls for a surgical instrument such as described in the embodiments herein may be incorporated into a foot operable mechanism in order to free the hands of the operator.

Figure 14:
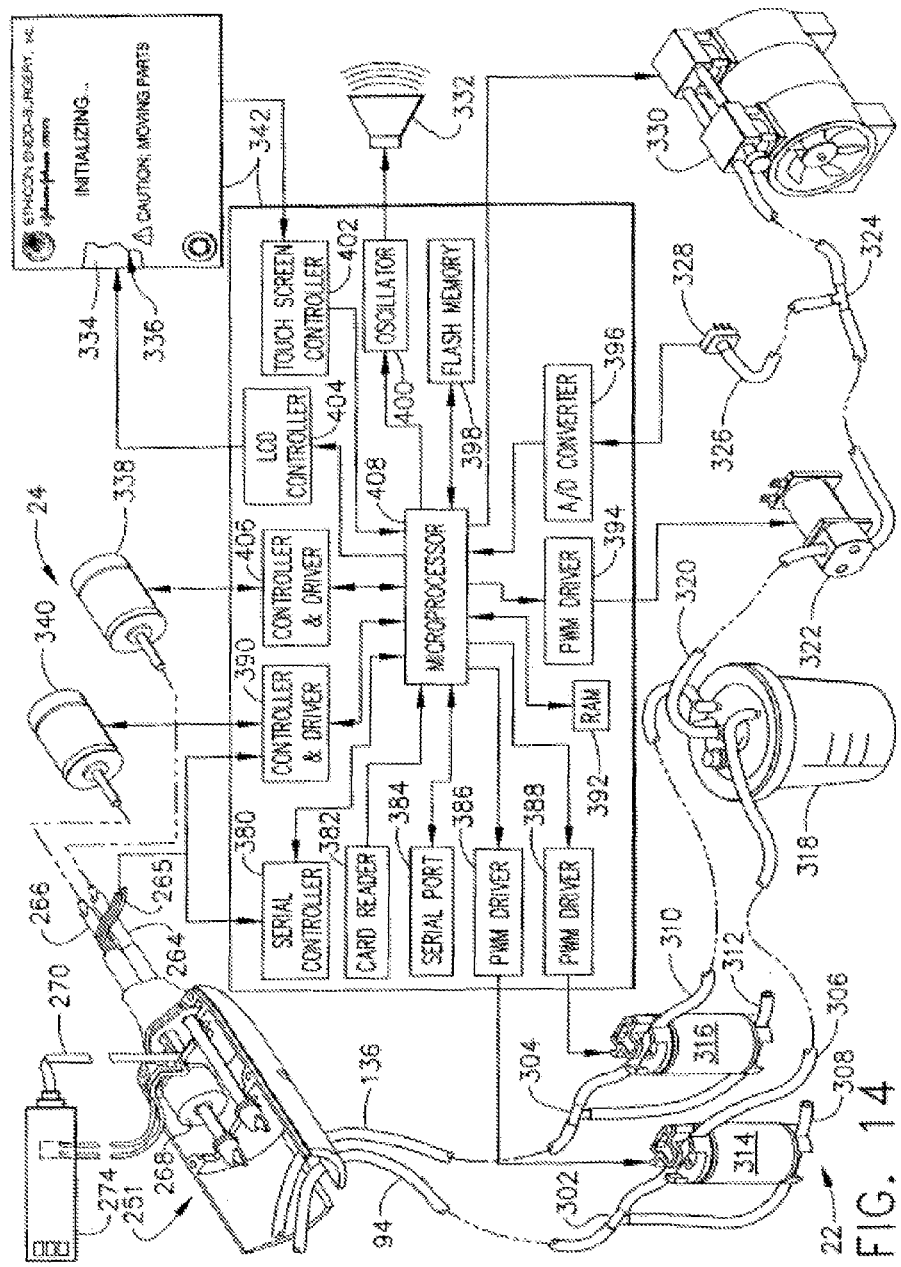
FIG. 14 is a schematic diagram of a control unit according to the present invention.
Figure 16A:
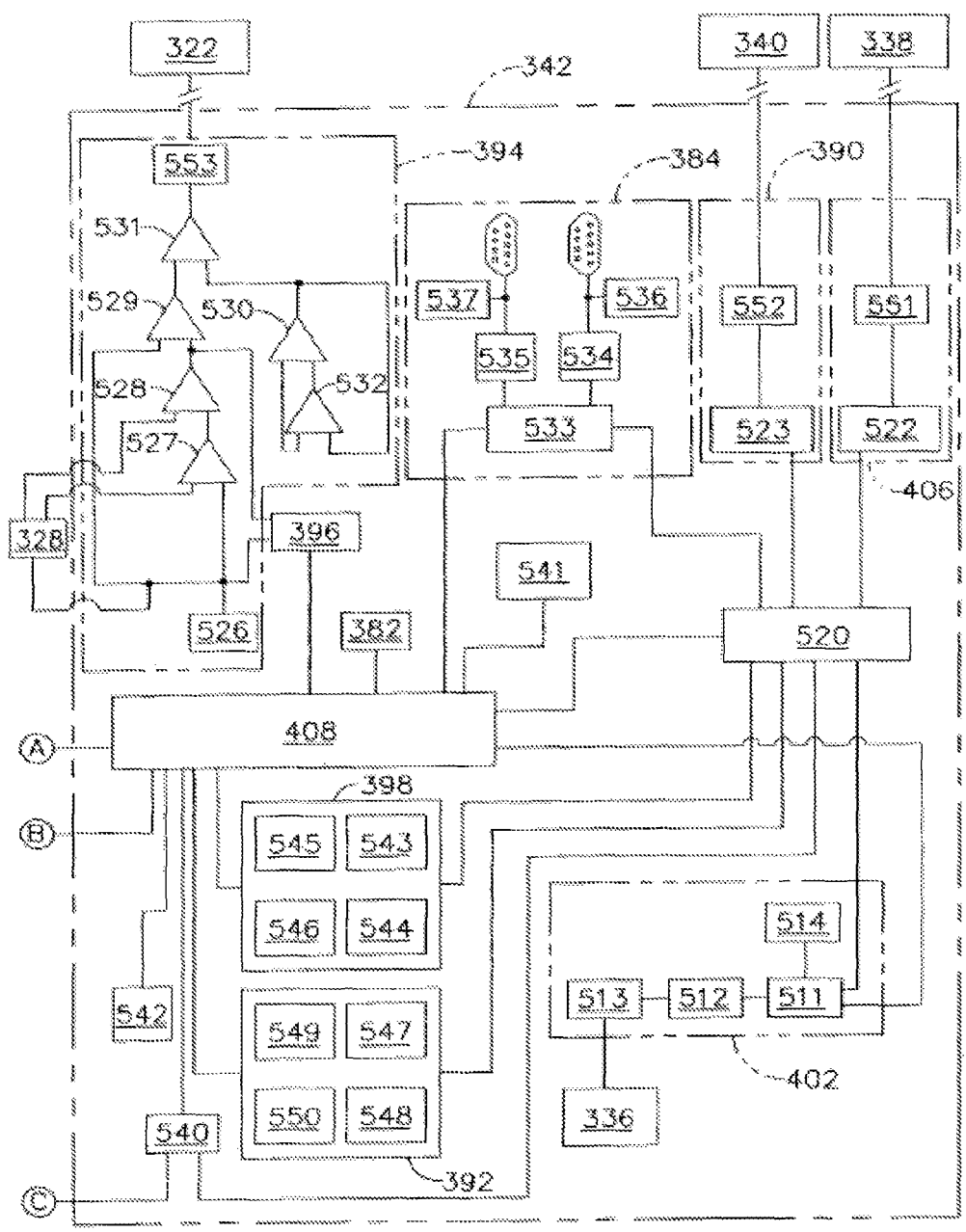
FIG. 16A is the first of two portions of a divided schematic diagram of the control unit components illustrated in FIG. 14.
Figure 16B:
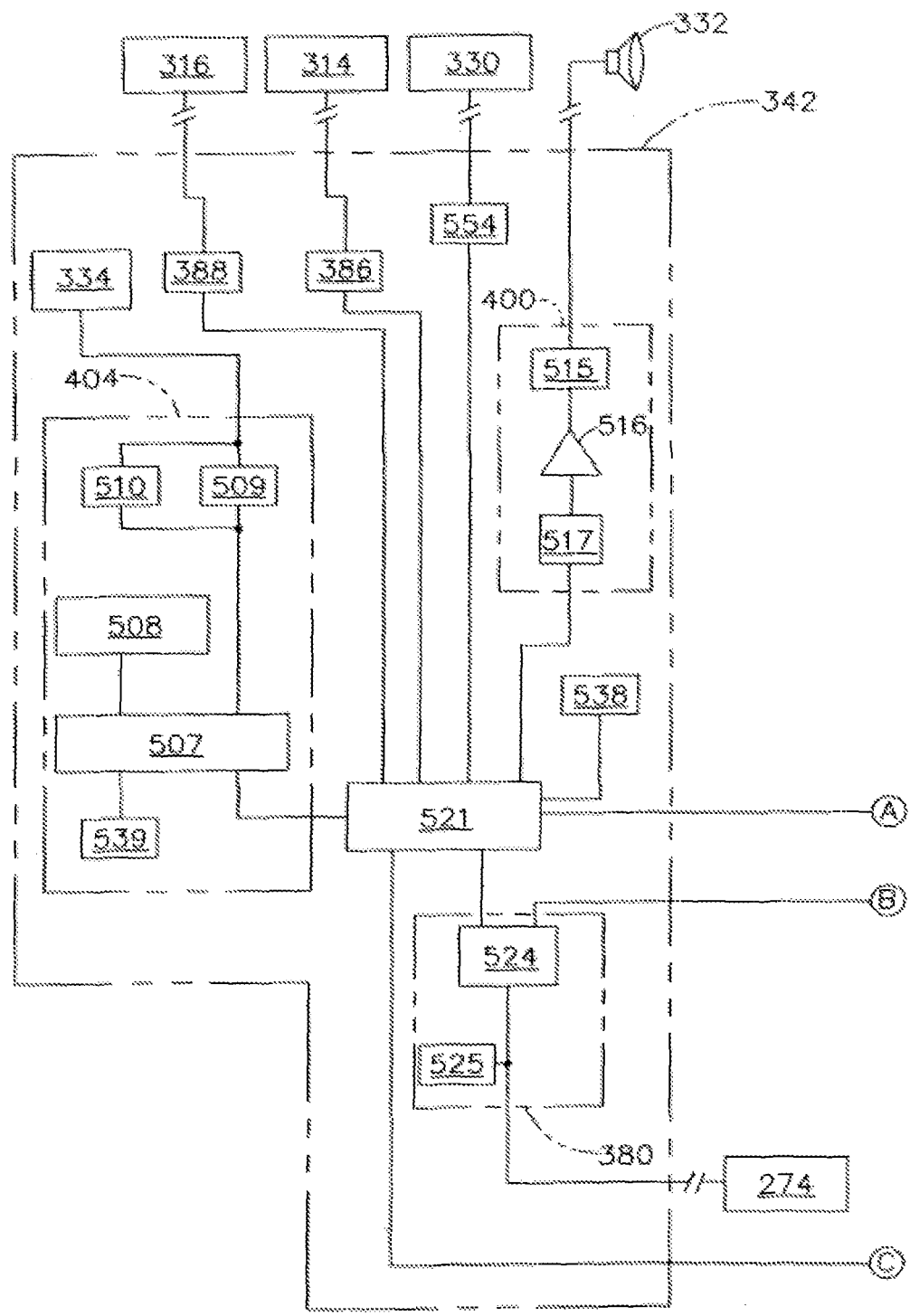
FIG. 16B is the second of two portions of the divided schematic diagram of the control unit components illustrated in FIG. 14.

FIG. 14 is a schematic diagram which illustrates the interconnection of the electro-mechanical components of the biopsy device to control unit 342. FIG. 14 illustrates the biopsy device illustrated in FIG. 1 and comprises control unit 342, fluid collection system 22, power transmission source 24, and handpiece 20 (see FIG. 1). A more detailed schematic diagram illustrating the elements of control unit 342 is shown in FIGS. 16A and 16B and will be described later. All of the components of FIG. 14 may be packaged into a portable, wheeled unit, and moved from room to room such as in a physician's office. Handpiece 20 (see FIG. 1), as described earlier, may be mounted to a stereotactic table already in the room, or handheld and used in combination with a handheld imaging device such as a handheld ultrasonic imager. Each time the biopsy device is used for a new patient, a new sterile probe assembly 40 may be used in handpiece 20.

In particular, FIG. 14 illustrates the interconnection of switchboard modified holster 251 with control unit 342, and the connection of power transmission source 24 to control unit 342. In the embodiment of the invention illustrated in FIG. 14, power transmission source 24 comprises a rotation motor 338 and a translation motor 340. Rotation motor 338 and translation motor 340 transmit rotational power to switchboard-modified holster 251 via first and second rotatable shafts, 264 and 266, respectively. An example of a motor which is suitable for either rotation motor 338 or translation motor 340 is available from Micro Motors Electronics, Incorporated, as DC Micro Motors Series 3863, with integral, miniature optical encoder, Part Number SHE 17. Rotation motor 338 has an integral rotation sensor also referred to as a first sensor. Translation motor 340 has an integral rotation sensor also referred to as a second sensor.

By having encased rotation sensor 268, as shown in FIG. 14, mounted in switchboard modified holster 251, it is possible for control unit 342 to calculate the amount of twisting along the length of second rotatable shaft 266 by comparing the output of the encoder of translation motor 340 to the output of encased rotation sensor 268. Since the number of revolutions of rotatable shaft 266 is used to determine where cutter 96 is located axially, this twisting could cause significant error, especially if rotatable shaft 266 is very long. This error could result, for example, in cutter 96 not stopping immediately when translation motor 340 is turned off, because first rotatable shaft 266 is continuing to "unwind". As a result, control unit 342 uses the signals from the integral rotation sensor (also referred to as the first sensor) of translation motor 340 and encased rotation sensor 268 to calculate accurately the axial position of cutter 96.

Second rotatable shaft 266 runs parallel to first rotatable shaft 264 between control unit 342 and holster 251. The mechanical efficiency of either shaft in transmitting rotation from the respective motor to holster 251 varies to some degree with the orientation of the rotatable shaft. If for example, it is necessary during the surgical procedure for the operator to drape first and second rotatable shafts, 264 and 266, so that they are bent significantly, then there will be more frictional energy losses than if the shafts were straight. In one embodiment of the present invention, if the initial current supplied to rotation motor 338 is not sufficient to attain a predetermined cutter rotational speed, the current to rotation motor 338 increases until a desired rotational speed is reached. The rotation sensor integrated into rotation motor 338 provides feedback signals to control unit 342, so that the compensating current can be supplied to rotation motor 338. Once the desired rotational speed is reached, the current to rotation motor 338 is "locked" until cutter 96 reaches position four at the end of its translation. This electrical compensation occurs for each time cutter 96 translates between the second and third positions, before cutter 96 begins to cut tissue. This allows for variations in the way rotatable shafts, 264 and 266, are oriented for each time the operator positions the biopsy instrument for collecting a tissue sample.

Referring now to fluid collection system 22 shown in FIG. 14, fluid collection system 22 comprises a first valve 314, a second pinch valve 316, a fluid collection canister 318, a regulator valve 322, a pressure sensor 328, and a vacuum pump 330. These components are interconnected to each other, control unit 342, and probe assembly 40 (FIG. 1) as follows. First vacuum tube 94 comes from probe assembly 40 (FIG. 1), and is attached to a first vacuum Y-connector 302 which is fluidly connected to a first upper line 306 and a first lower line 308. The two lines, 306 and 308, pass through first pinch valve 314. An example of a suitable, commercially available, three-way pinch valve for this application is Model Number 373 12-7 15, available from Angar Scientific Company, Incorporated. Pinch valve 314 closes either the first upper line 306 or the first lower line 308, but never both lines simultaneously. First lower line 308 provides a vent to atmospheric pressure. First upper line 306 attaches to fluid collection canister 318. Similarly, second vacuum line 136 from probe assembly 40 attaches to a second Y-connector 304 which is fluidly connected to a second upper line 310 and a second lower line 312. The first and second vacuum Y-connectors, 302 and 304, may be molded from a rigid polymer such as polycarbonate. Second upper line 310 passes through a second pinch valve 316, which is identical to the first, and to canister 318. Second lower line 312 passes through second pinch valve 316 and vents to the atmosphere. Again, only one or the other of the two lines, 310 and 312, may be pinched closed at any time.

Still referring to fluid collection system 22 of FIG. 14, a main vacuum line 320 attaches canister 318 to electrically powered vacuum pump 330. An example of a suitable vacuum pump for this application is available as WOB-L PISTON Series 2639 from Thomas Compressors and Vacuum Pumps, Incorporated. Main vacuum line 320 passes through regulator valve 322 to adjust electronically the vacuum pressure supplied to canister 318. An example of a commercially available regulator valve for this application is model number VSONC6S11VHQ8 from Parker Hannifin Corporation, Pneutronics Division. Pressure sensor 328 is fluidly attached to main vacuum line 320 at a sensor connection 324. The signal from pressure sensor 328 is sent to an A/D converter 396 of control unit 342. An example of a commercially available, compensated pressure sensor for this application is model number SDX15 from SenSym, Incorporated.

In FIG. 14 control unit 342 is shown to include the elements inside the drawn box, a liquid crystal display (LCD) 334, and a touchscreen 336. FIGS. 16A and 16B together form a detailed schematic of the elements of control unit 342. FIGS. 14, 16A, and 16B may be referred to concurrently for the description of the elements of control unit 342. At the heart of control unit 342 is a microprocessor 408. An example of a suitable microprocessor 408 is 40 MHz, 32-bit microprocessor, available from Motorola, Incorporated as Part Number XCF5206EFT40. Microprocessor 408 is designed to perform logic operations that may be translated into simple electromechanical actions. LCD 334 prompts and informs the operator during the operation of the biopsy device. A suitable example for LCD 334 is 640.times.480 color TFT-LCD display available from Sharp Electronics Corporation as part number LQ64D343. A resistive touch screen 336 covers LCD 334 for the user interface. An example of a suitable touch screen 336 is available from Dynapro Thin Film Products, Incorporated as Part Number 95638. LCD 334 is electronically connected to a touch screen controller 402 in control unit 342.

Interfacing with microprocessor 408 is an oscillator 540, an EPROM 542, and a voltage supervisor 541. Oscillator 540 is available, for example, as Part Number ASV-40.000000-PCSA (40 megahertz) from Abracon Corporation. A suitable example for EPROM 542 is Part Number AT27BV4096-15JC available from Atmel Corporation. A suitable example for voltage supervisor 541 (for a 2.93-volt supply) is available as Part Number TLC7731D from Texas Instruments, Incorporated.

Touch screen controller 402 allows control unit 342 to respond to the user's touch by interpreting touch inputs. Other more conventional devices, such as mechanical switches, may be used instead of touch screen controller 402 for controlling control unit 342. Touch screen controller 402, however, is easy to keep clean and is intuitive for the operator to use. Touch screen controller 402 comprises a microcontroller 511, an A-D converter 512, a multiplexer-demultiplexer 513, and an EEPROM 514. A suitable example for microcontroller 511 is 8-bit micro-controller Part Number 95705 from Microchip Technology, Incorporated. A suitable example for A-D converter 512 is 10-bit serial A-D converter Part Number TLV1543CDW from Texas Instruments, Incorporated. A suitable example for multiplexer-demultiplexer 513 is dual 4-to-1 line analog multiplexer-demultiplexer Part Number MC74HC4052D from Motorola, Incorporated. A suitable example for EEPROM 514 is 1K-bit serial EEPROM Part Number 93AA46SN from Microchip Technology, Incorporated.

A LCD controller 404 is provided to interface between microprocessor 408 and LCD 334. LCD controller 404 reduces the burden of microprocessor 408 by efficiently controlling display parameters such as color, shading, screen update rates, and it typically accesses the memory chips of microprocessor 408 directly. LCD controller 404 comprises a 25-megahertz oscillator 539 that is available, for example, as part number ASV-25.000000-PCSA from Abracon Corporation. LCD controller 404 also comprises an LCD/CRT controller 508 that is available, for example, as part number SED1354FOA from Seiko Epson Corporation, and a 1-meg-.times.16-bit, 60 nanosecond, EDO DRAM 507 that is available, for example, as part number MT4LC1M16E5TG-6 from Micron Technology, Incorporated. LCD controller 404 further comprises a pair of 16-bit drivers, 509 and 510, of the non-inverting, buffer-line type, that are available, for example, as part number 74ACTQ16244SSCX from National Semiconductor Corporation.

A miniature annunciator 332 is provided with control unit 342 in order to provide the operator with audible feedback "beeps" upon each activation of an icon control on LCD 334. An example of a suitable annunciator for this application is model number EAS-45P104S from Matshusita Electric Corporation of America (Panasonic Division). Annunciator 332 interfaces with microprocessor 408 by an oscillator 400 which converts the digital input signal from microprocessor 408 to an analog, periodic output signal, thus controlling the audio frequency of annunciator 332. The volume of the sound coming from annunciator 332 is controllable, as will be described later. Referring to FIG. 16B, oscillator 400 comprises a 62 dB audio attenuator 517 that is available, for example, as Part Number LM1971M from National Semiconductor Corporation. Oscillator 400 further comprises an operational amplifier 516 that may be identical, for example, to operational amplifier 530 already described. Oscillator 515 further comprises a power audio amplifier 515 that is available, for example, as part number LM486M from National Semiconductor Corporation.

Still referring to control unit 342 shown in FIGS. 14, 16A and 16B, a first motor controller and driver 390 interfaces with translation motor 340 and with microprocessor 408. Translation motor 340 is operationally connected to second rotatable shaft 266. Controller and driver 390 converts digital input signals from microprocessor 408 into analog motor input signals for controlling motor rotational direction and speed. Closed loop digital speed control of translation motor 340 is also achieved within controller and driver 390 using feedback signals from encased rotation sensor 268 in holster 251 and rotation sensor integrated within translation motor 340. First motor controller and driver 390 comprises a first H-bridge motor driver 552 (also referred to as a first driver) and a first motor controller 523. A suitable example of a first H-bridge motor driver is available as Part Number LMD18200T from National Semiconductor Corporation. A suitable example of a motor controller is available as Part Number LM629M-8 from National Semiconductor Corporation.

Still referring to FIGS. 14, 16A, and 16B, rotation motor 338 drives first rotatable shaft 264. Rotation motor 338 interfaces with microprocessor 408 through second controller and driver 406 which comprises a second H-bridge motor driver 551 (also referred to as a second driver) and a second motor controller 522. Second H-bridge motor driver 551 may be identical to first H-bridge motor driver 552, already described. Second motor controller 522 may be identical to first motor controller 523, already described. Microprocessor 408 via second controller and driver 406 continually calculates and updates the rotational positions of cutter 96, as well as the rotational speed and acceleration, using feedback signals from the rotation sensor integrated within rotation motor 338.

Still referring to control unit 342 shown in FIGS. 14, 16A, and 16B, a serial controller 380 is electronically connected to switchboard 274 by ribbon cable 270 and control cord 265. Ribbon cable 270 is contained within holster 251. Control cord 265 runs along, and may be attached to, first rotatable shaft 264 and second rotatable shaft 266. Serial controller 380 coordinates information exchange across the serial communication link between switchboard 274 and microprocessor 408. An optional card reader 382 may be provided in control unit 342 for reading data from memory card in order to facilitate future software upgrades and servicing. A serial port 384 is provided for the bi-directional data exchange in a serial transmission mode, again to facilitate future software upgrades and servicing. Serial controller 380 includes a quad differential line receiver 524 that is available, for example, as Part Number DS90C032™ from National Semiconductor Corporation. Serial controller 380 further includes an ESD (electrostatic discharge) over-voltage protection array 525 that is available, for example, as Part Number SP723AB from Harris Semiconductor Products.

A first PWM (pulse width modulation) driver 386 interfaces first pinch valve 314 with microprocessor 408. First PWM driver 386 converts a digital input signal from microprocessor 408 to an analog output signal having a wave of fixed frequency and amplitude, but varying duty cycle. To drive the solenoid in pinch valve 314, PWM driver 386 is used when the duty cycle is high to initially move the solenoid. Once pinch valve 314 is actuated, the duty cycle is reduced to a level, which maintains valve position, thus minimizing power requirements. A second PWM driver 388 similarly interfaces a second pinch valve 316 with microprocessor 408. A suitable example for both first PWM driver 386 and second PWM driver 388 is FET (60 volt, 3.5 amp, 0.10 ohm, N-channel dual) Part Number NDS9945 available from Fairchild Semiconductor Corporation.

Referring to FIG. 16B, a first EPLD (Erasable Programmable Logic Device) 521 interfaces with LCD controller 404, PWM driver 388, PWM driver 386, an FET 554, oscillator 400, a first 8 MHz. oscillator 538, serial controller 380, and microprocessor 408 (via the path represented by the encircled "A"). A suitable example for first EPLD 521 is available as Part Number EPM7256ATC144-7 from Altera Corporation. FET 554 may be identical, for example, to FET 556 of second PWM driver 388. First oscillator 538 is available, for example, as Part Number ASL-8.000000-PCSA from Abracon Corporation.

A second EPLD 520 interfaces microprocessor 408 with serial port 384, first controller and driver 390, second controller and driver 406, touch screen controller 402, RAM 392, flash memory 398, and oscillator 540. EPLD 520 is capable of operating at 166.7 megahertz and is available, for example, as Part Number EPM7256ATC144-7 from Altera Corporation.

A third PWM driver 394 interfaces with regulator valve 322 and A/D converter 396. PWM driver 394 comprises a voltage reference device 526 comprising a first operational amplifier and a voltage reference. PWM driver 394 further comprises a second operational amplifier 527, a third operational amplifier 528, a fourth operational amplifier 529, a fifth operational amplifier 530, a sixth operational amplifier 531, and a seventh operational amplifier 532. The operational amplifier in voltage reference device 526, and operational amplifiers 527, 528, 529, 530, 531, and 532 are more descriptively referred to as "Quad Rail-to-Rail Operational Amplifiers". A suitable example for each is available as Part Number LMC6484IM from the National Semiconductor Corporation. PWM driver 394 further comprises a first FET (Field Effect Transistor) 553. A suitable example of FET 553 is available as Part Number NDS9945 (60 volt, 3.5 amp, 0.10 ohm, N-channel dual) from Fairchild Semiconductor Corporation.

A RAM (Random Access Memory) memory device 392 (also referred to as a temporary memory device) is provided with microprocessor 408, and inherently loses stored data when power is removed. A flash memory device 398 (also referred to as a non-volatile memory device), on the other hand, is provided with microprocessor 408 to store data even without power, but it has slower access time than RAM memory device 392. RAM memory device 392 comprises four EDO DRAM devices, 547, 548, 549, and 550. These devices may be identical and a suitable example of each is available as Part Number MT4LC1M16E5TG-6 from Micron Technology, Incorporated. Flash memory device 398 comprises four RAM devices which may be identical and a suitable example of each is available as Part Number AM29LV800BT-70REC from Advanced Micro Devices, Incorporated. The combination of the RAM memory device (temporary memory device) 392, the flash memory device (non-volatile memory device) 398, and microprocessor 408 is sometimes referred to simply as a computing device. The computing device may also include first controller 523 and second controller 522 in an alternate embodiment.

Serial port 384 comprises a dual, universal, asynchronous receiver/transmitter 533 available, for example, as part number ST16C2552CJ44 from Exar Corporation. Serial port 384 further comprises a first driver-receiver 534 and a second driver-receiver 535, each more descriptively called a "TIA/EIA-232, 3.times.5 driver-receiver" and available, for example, as Part Number DS14C335MSA from National Semiconductor Corporation. Serial port 384 further includes a first transient suppressor 536 and a second transient suppressor 537, each a bi-directional, 24 volt, 300 watt unit available, for example, as Part Number SMDA24C-8 from General Semiconductor, Incorporated.

Location for an optional card reader 382 interfacing with microprocessor 408 is also shown in FIG. 16A. Card reader 382 may be used in future embodiments of the biopsy device to program control unit 342 with alternate values, for example, of the desired translation and rotation speeds of cutter 96.

An A/D converter 396 converts voltage signals from pressure sensor 328 into digital signals which are transmitted to microprocessor 408, and used by microprocessor 408 to maintain a desired vacuum pressure in fluid collection system 22. A suitable example of A/D converter 396 is ADC-DAC, 8-bit, I2C bus interface available as Part Number PCF8591AT from Philips Electronics N.V.

The biopsy device is provided with a conventional, 48-volt DC power supply used in combination with standard DC-to-DC converters and electrical voltage regulators in order to supply reduced voltages to the components of control unit 342.

Microprocessor 408 may be used to monitor the output value of second controller and driver 406 PID filter such that if the output of it exceeds a predefined maximum value, the translational speed of cutter 96 is reduced a set amount by sending an updated speed command to first controller and driver 390. This closed-loop system insures that the desired cutter rotational speed is maintained by decreasing the translational speed of cutter 96. This automatic adjustment to cutter translational speed occurs when cutter rotational resistance becomes abnormally high. Cutter rotational resistance is the combination of cutting resistance (when cutter 96 encounters obstructions, very dense tissue, or calcified lesions, for example) and mechanical resistance (when the operator, for example, manipulates piercer 70 into tissue with enough force to place a significant bending moment on piercer 70 so that cutter 96 binds inside piercer lumen 80). Rather than attempting to maintain cutter translational speed by ramping up cutter rotational speed, the cutter translational speed is decreased in order to reduce the cutter rotational resistance. In one embodiment of the present invention, this is accomplished in the following manner. While in the sampling mode and with cutter 96 advancing toward the third position (proximal to port 78), when cutter 96 reaches a predetermined translational position, microprocessor 408 sends a signal to second controller and driver 406 to initiate cutter rotation. The rotational speed of cutter 96 follows a predefined speed profile which insures that the cutter rotational speed is at a predetermined Q (also referred to as predetermined rotational speed) revolutions per minute (rpm) when cutter 96 reaches the third position. When cutter 96 reaches the third position, microprocessor 408 sends a signal to first controller and driver 390 to advance cutter 96 at a predetermined translation speed T (also referred to as a third, predetermined translation speed) inches per second (in/sec). Cutter 96 then progresses through port 78 at predetermined translation speed T in/sec while rotating at velocity Q rpm. While advancing through port 78, cutter 96 rotational speed is monitored by second controller and driver 406, using signals from the rotation sensor integrated within rotation motor 338. If the rotational speed is greater than Q rpm, electrical current to translation motor 340 is increased. If the cutter rotational speed is less than Q rpm, electrical current to translation motor 340 is decreased.

If it is desired to control the speed of either translation motor 340 or rotation motor 338 in response to increased cutter rotation resistance, such as in a further embodiment of the present invention, one way to do so is to generate an error signal based on the difference between the desired speed (translation or rotation, depending on which motor is controlled) and the actual speed. The error signal is then input into a proportional, integral, and derivative (PID) digital filter, which is part of the respective controller and driver, either first controller and driver 390, or second controller and driver 406. The sum of these three terms is used to generate the pulse width modulation (PWM) signal. First and second controller and driver, 390 and 406, each generate the error signal and the PWM signal. A PWM signal is input to first controller and driver 390 to generate an analog output signal to drive translation motor 340. Similarly, a PWM signal is input to the second controller and driver 406 to generate an analog output signal to drive rotation motor 338.

Figure 15:
FIG. 15 is an enlarged view of an LCD display illustrated in FIG. 14.

FIG. 15 is an enlarged view of LCD 334 on which messages are displayed during the calibration procedure of the biopsy system. LCD 334 includes a touch screen 336. LCD 334 and touch screen 336 are part of control unit 342 of FIG. 14.

As described earlier, during operation of the present invention cutter 96 translates between a fully retracted position just proximal to tissue sampling surface 64, also referred to as position 1 (see FIGS. 6A and 6B), to a fully deployed position just distal to port 78, also referred to as position 4 (see FIGS. 8A and 8B). Because of manufacturing and assembly differences inherent in each probe assembly 40 it is necessary for control unit 342 to "learn" the location of positions 1 and 4 upon start-up for each new probe assembly 40 operationally connected to holster 140. Once positions 1 and 4 are established all intermediate positions are readily calculated by control unit 342. It is also desirable at initial start-up to rotate cutter 96 to determine if it is operating within a pre-established acceptable speed range without subject to excessive friction or "drag".

Figure 17A:
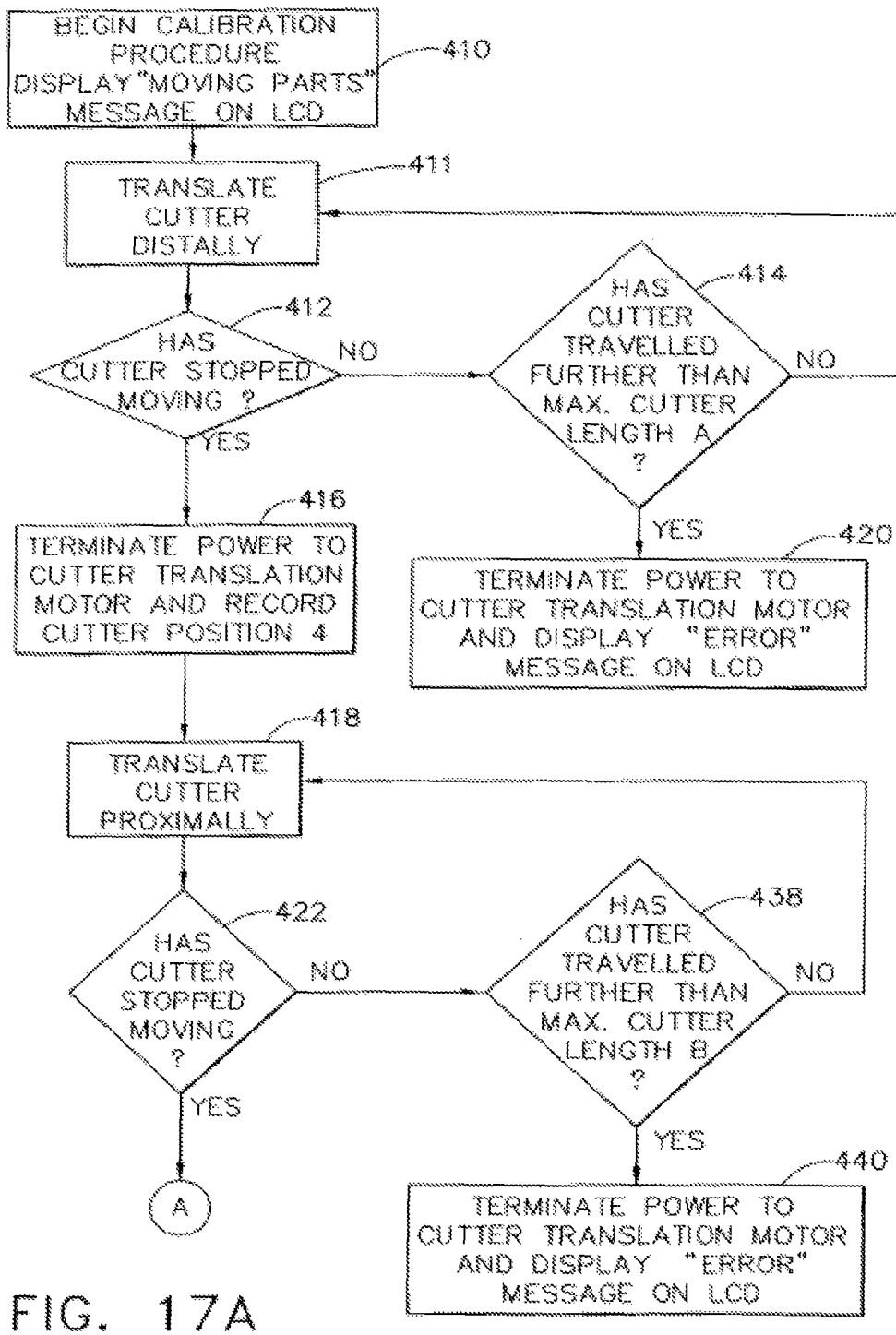
FIG. 17A is a first portion of a flow chart pertaining to a calibration method of a biopsy system according to the present invention, specifically the cutter translation and position.
Figure 17B:
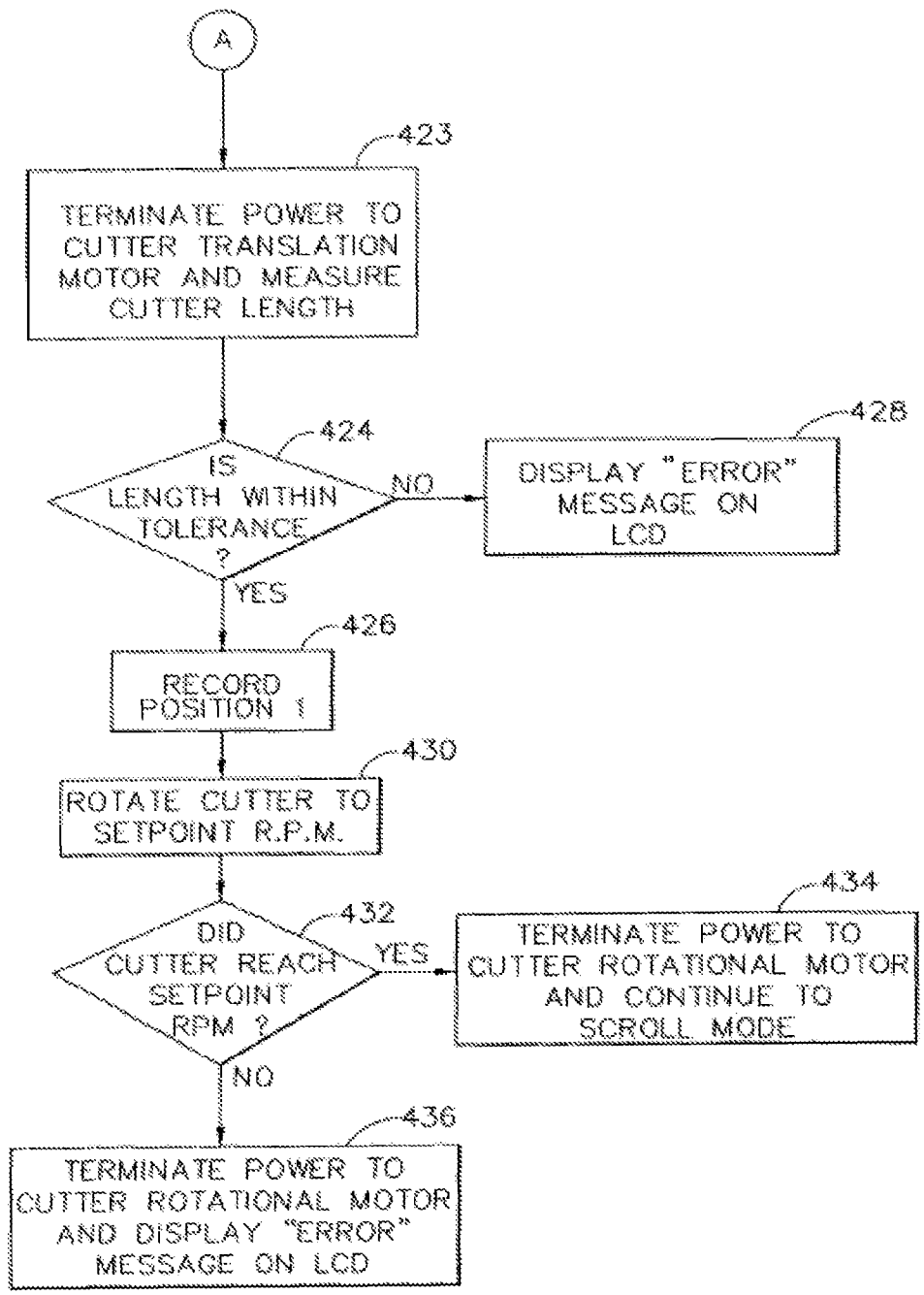
FIG. 17B is a second portion of a flow chart pertaining to a calibration method of a biopsy system according to the present invention, specifically continuing the cutter translation and position and including cutter rotation.

FIGS. 17A and 17B illustrate a flow diagram for a method of calibration according to the present invention. The steps of the calibration method are represented in the flow chart. Even though each box may represent more than one step, or may only be part of a step, each box is referred to simply as a step. Progression of the steps occurs generally in the direction of the arrows connecting the boxes.

Referring first to FIG. 17A, step 410 represents the beginning of the calibration method. Upon start-up the user is prompted on LCD 334 (see FIG. 14) to select a probe size. The user does so by touching the appropriate icon on touch screen 336. At step 410 a screen appears on LCD 334 warning of moving parts. At step 411 first controller 523 signals first H-bridge motor driver 552 to supply current to translation motor 340 causing cutter 96 to translate distally toward position 4 (see FIGS. 8A and 8B). Screw 114 rotates in a direction to cause carriage 124 to move cutter 96 distally.

At step 412 control unit 342 is monitoring the movement of cutter 96 by way of signals from encased rotation sensor 268. At step 414, cutter translation continues as long as the cutter travel distance is less than maximum cutter length "A" programmed into first controller 523 in control unit 342. In the present embodiment the value of maximum cutter length "A" is 5.25 inches, based upon initial user input for probe size. If, as the cutter continues its distal translation, the cutter distance traveled exceeds maximum cutter length "A", first controller 523 signals first H-bridge motor driver 552 to terminate current to translation motor 340 and an error message is displayed on LCD 334 at step 420.

Again referring to step 412, as cutter 96 continues to translate distally and as long as the distance traveled does not exceed maximum cutter length "A", eventually distal carriage wall 123 contacts distal screw support wall 49 halting the translation of cutter 96. This event forces the rotation of screw 114 to stop. Current is terminated to translation motor 340 and encased rotation sensor 268 sends a signal to first controller 523 which records position 4 at step 416.

After successful completion of step 416, at step 418 first controller 523 signals first H-bridge motor driver 552 to reverse rotation of translation motor 340, likewise screw 114 reverses rotation, sending cutter 96 in a proximal direction toward position 1 (see FIGS. 6A and 6B).

At step 422 control unit 342 is again monitoring the movement of cutter 96. At step 438, cutter translation continues as long as the cutter travel distance is less than maximum cutter length "B" programmed into first controller 523 in control unit 342. In the present embodiment the value of maximum cutter length "B" is 5.10", based upon initial user input for probe size. If, as the cutter continues its proximal translation, the cutter distance traveled exceeds maximum cutter length "B", first controller 523 signals first H-bridge motor driver 552 to terminate current to translation motor 340 and an error message is displayed on LCD 334 at step 440.

Again referring to step 422, as cutter 96 continues to translate proximally and as long as the distance traveled does not exceed maximum cutter length "B", eventually proximal carriage wall 125 contacts proximal screw support wall 55 halting the translation of cutter 96. This event forces the rotation of screw 114 to stop. Encased rotation sensor 268 sends a signal to first controller 523. Current is terminated to translation motor 340 at step 423 (see FIG. 17B) and the distance traveled by cutter 96 between position 4 and position 1 is recorded in control unit 342. At step 424, if the cutter translation distance is not within a predetermined length tolerance, 5.025"+/−0.075" for the present embodiment, based upon initial user input for probe size, an error message is displayed on LCD 334 at step 428. Again referring to step 424, if the cutter translation distance is within the 5.025"+/−0.075" length tolerance, first controller 523 records position 1 at step 426.

Cutter positions 4 and 1 have now been recorded in control unit 342 for this specific sterile probe assembly 40/handpiece 20 combination. Slight length variations due to manufacturing and assembly tolerances from one sterile probe assembly to another have been effectively compensated for by this calibration procedure.

Also, as discussed earlier, at step 424 control unit 342 will compute the distance traveled by cutter 96 between its most distal position and most proximal position and compare that value with a value pre-programmed into the memory of control unit 342, to determine if the correct probe size is selected for the software residing in the memory of control unit 342. If the computed value and pre-programmed values do not agree, an error message is displayed on LCD 334 at step 428.

Also, subsequent to the previously described calibration method and during the actual biopsy procedure control unit 342 uses the values recorded for positions 4 and 1 to calculate the desired distal and proximal stop points for cutter 96. In the present embodiment, during distal translation current is terminated to translation motor 340 when cutter 96 is 0.007" short of reaching position 4. During proximal translation, current is terminated to translation motor 340 when cutter 96 is 0.006" short of reaching position 1. This effectively eliminates the risk of distal and proximal carriage walls, 123 and 125 respectively, impacting the distal and proximal screw support walls, 49 and 55 respectively, eliminating the potential for twisting and "winding" of the flexible, rotatable drive cables.

Again referring to FIG. 17B, at step 430 (while cutter 96 is at position 1) second controller 522 signals second H-bridge driver 551 to supply current to rotation motor 338 which causes cutter 96 to rotate. Current supply is adjusted to the rotation motor 338 in an effort to maintain a pre-determined cutter rotational speed. In the present embodiment the pre-determined rotational speed is 200 revolutions per minute (rpm). Actual speed of rotation motor 338 is monitored by second controller 522 by way of position feedback provided from the integral rotation sensor in rotation motor 338. The difference between the commanded position and actual position are continually compared by microprocessor 408. Monitoring this difference is a means of establishing the amount of rotational resistance rotational motor 338 is experiencing due to system frictional losses. The larger the difference the greater the system friction, possibly indicating faulty system components. At step 432 second controller 522 continually adjusts current to rotation motor 338 to reach and maintain a speed of 200 rpm for a fixed interval of time. For the present embodiment the fixed interval of time is 3 seconds.

At step 436 second controller 522 adjusts current supply to rotation motor 338 in an effort to reach and maintain 200 rpm. If, in doing so, a predetermined error count (difference between commanded and actual positions, which for the present embodiment is 1200 encoder counts) is exceeded before the fixed interval of time is reached, as soon as the error count is exceeded current is terminated to rotation motor 338 and an error message is displayed on LCD 334.

If, however, rotation motor 338 speed is maintained at 200 rpm for the fixed interval of time (3 seconds) without exceeding the predetermined error count, current is terminated to rotation motor 338 and "scroll mode" is displayed on LCD 334 at step 434.

The biopsy system is now calibrated and ready for the next operating mode.

While preferred embodiments of the present invention have been shown and described herein, it will be obvious to those skilled in the art that such embodiments are provided by way of example only. Numerous variations, changes, and substitutions will now occur to those skilled in the art without departing from the spirit and scope of the appended claims.

We claim:

1. A biopsy system comprising:
   a. a plurality of disposable probe portions, the plurality of disposable probe portions having various size attributes, wherein at least one of the plurality of disposable probe portions comprises:
      i. an elongated hollow piercer having a lateral tissue receiving port, and
      ii. a cutter rotatable and axially translatable relative to the lateral tissue receiving port;
   b. a reusable portion, wherein the reusable portion is adapted to receive at one of the plurality of disposable probe portions; and
   c. a control unit, wherein the control unit is operable to control at least one of the plurality of disposable probe portions, wherein the control unit is operable to determine the size attributes of the at least one of the plurality of disposable probe portions.

2. The biopsy system of claim 1, wherein the size attributes comprise different diameter sizes of the piercer.

3. The biopsy system of claim 1, wherein the size attributes comprise different lengths of the piercer.

4. The biopsy system of claim 1, wherein the size attributes are communicated to the control unit by a user input.

5. The biopsy system of claim 1, wherein the size attributes are determined by the control unit by translating the cutter from a first position to a second position and computing a distance between the first position and the second position.

6. The biopsy system of claim 5, wherein the control unit compares the size attributes determined by the control unit to size attributes communicated to the control unit by a user input.

7. The biopsy system of claim 1, wherein the biopsy system comprises a plurality of operating modes, and wherein at least one of the plurality of operating modes is dependent on the size attributes of the disposable probe portion.

8. The biopsy system of claim 7, wherein one of the plurality of operating modes comprises a calibration mode.

9. The biopsy system of claim 7, wherein one of the plurality of operating modes comprises a sampling mode.

* * * * *